United States Patent
Afshar

(10) Patent No.: US 11,066,460 B2
(45) Date of Patent: Jul. 20, 2021

(54) PHAGE DISPLAY VECTORS AND METHODS OF USE

(71) Applicant: Eli Lilly and Company, Indianapolis, IN (US)

(72) Inventor: Sepideh Afshar, Del Mar, CA (US)

(73) Assignee: Eli Lilly and Company, Indianapolis, IN (US)

( * ) Notice: Subject to any disclaimer, the term of this patent is extended or adjusted under 35 U.S.C. 154(b) by 272 days.

(21) Appl. No.: 15/775,892

(22) PCT Filed: Nov. 18, 2016

(86) PCT No.: PCT/US2016/062806
§ 371 (c)(1),
(2) Date: May 14, 2018

(87) PCT Pub. No.: WO2017/091467
PCT Pub. Date: Jun. 1, 2017

(65) Prior Publication Data
US 2018/0327480 A1 Nov. 15, 2018

Related U.S. Application Data

(60) Provisional application No. 62/259,801, filed on Nov. 25, 2015.

(51) Int. Cl.
*C07K 16/00* (2006.01)
*C07K 14/005* (2006.01)
*C12N 7/00* (2006.01)
*C12N 15/70* (2006.01)

(52) U.S. Cl.
CPC .......... *C07K 16/005* (2013.01); *C07K 14/005* (2013.01); *C12N 7/00* (2013.01); *C12N 15/70* (2013.01); *C12N 2795/14122* (2013.01); *C12N 2795/14131* (2013.01)

(58) Field of Classification Search
CPC .............................. C07K 16/005; C07K 14/005
See application file for complete search history.

(56) References Cited

U.S. PATENT DOCUMENTS

2014/0335016 A1* 11/2014 Krishnan ............... C07K 16/18
424/1.49

FOREIGN PATENT DOCUMENTS

WO 2002103012 A1 12/2002

OTHER PUBLICATIONS

Accession AFQ39731. 2013. p. 3 [synthetic construct] (Year: 2013).*
Jestin et. al. Improving the display of proteins on filamentous phage. Res. Microbiol. 152 (2001) 187-191 (Year: 2001).*
Sidhu et. al. High Copy Display of Large Proteins on Phage for Functional Selections. 2000 J. Mol. Biol. 296, 487-495 (Year: 2000).*
Nakayama G R et al: "Improving the copy numbers of antibody fragments expressed on the major coat protein of bacteriophage M13" Immunotechnology, Elsevier Science Publishers BV, NL, vol. 2, No. 3, Sep. 1, 1996, pp. 197-207.
Omidfar Kobra, et al: "Advances in phage display technology for drug discovery." Expert Opinion on drug discovery Jun. 2015, vol. 10, No. 6, Jun. 2015, pp. 651-669.
Russel et al., Introduction to Phage Biology and Display, Phage Display: A Laboratory Manual: Cold Harbor Lab. Press.
Methods in Molecular Biology, vol. 178, Antibody Phage Display: Methods and Protocols, edited by O'Brien and Aitken.
Lee et al., Biochemical and Biophysical Research Communications, 411 (2011); 348-353.
Handa et al., Rapid and Reliable Site-Directed Mutagenesis Using Kunkel's Approach, Methods in Molecular Biology, vol. 182: In Vitro Mutagenesis Protocols, 2nd Ed.
Wu, Simultaneous Humanization and Affinity Optimization of Monoclonal Antibodies, Methods in Molecular biology, vol. 2017. Recombinant Antibodies for Cancer Therapy: Methods and Protocols, edited by Weischof and Krauss.

* cited by examiner

*Primary Examiner* — Neil P Hammell
*Assistant Examiner* — Tiffany Nicole Grooms
(74) *Attorney, Agent, or Firm* — Robert L Sharp

(57) ABSTRACT

The present invention relates to vectors suitable for use in displaying proteins on the surface of bacteriophage M13 as fusion constructs with the surface protein P.III, bacteriophage M13 particles comprising a mutated P.III protein on the phage coat surface, as well as methods for producing bacteriophage M13 particles and methods for transfecting or infecting a host cell comprising the vectors and bacteriophage of the invention.

26 Claims, No Drawings

Specification includes a Sequence Listing.

SEQUENCE LISTING

<160> NUMBER OF SEQ ID NOS: 36

<210> SEQ ID NO 1
<211> LENGTH: 406
<212> TYPE: PRT
<213> ORGANISM: Artificial sequence
<220> FEATURE:
<223> OTHER INFORMATION: Synthetic Construct

<400> SEQUENCE: 1

Ala Glu Thr Val Glu Ser Cys Leu Ala Lys Ser His Thr Glu Asn Ser
1               5                   10                  15

Phe Thr Asn Val Trp Lys Asp Asp Lys Thr Leu Asp Arg Tyr Ala Asn
                20                  25                  30

Tyr Glu Gly Cys Leu Trp Asn Ala Thr Gly Val Val Val Cys Thr Gly
            35                  40                  45

Asp Glu Thr Gln Cys Tyr Gly Thr Trp Val Pro Ile Gly Leu Ala Ile
        50                  55                  60

Pro Glu Asn Glu Gly Gly Gly Ser Glu Gly Gly Gly Ser Glu Gly Gly
65                  70                  75                  80

Gly Ser Glu Gly Gly Gly Thr Lys Pro Pro Glu Tyr Gly Asp Thr Pro
                85                  90                  95

Ile Pro Gly Tyr Thr Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
        115                 120                 125

Gln Pro Leu Asn Thr Phe Met Phe Gln Asn Asn Arg Phe Arg Asn Arg
130                 135                 140

Gln Gly Ala Leu Thr Val Tyr Thr Gly Thr Val Thr Gln Gly Thr Asp
145                 150                 155                 160

Pro Val Lys Thr Tyr Tyr Gln Tyr Thr Pro Val Ser Ser Lys Ala Met
                165                 170                 175

Tyr Asp Ala Tyr Trp Asn Gly Lys Phe Arg Asp Cys Ala Phe His Ser
            180                 185                 190

```
Gly Phe Asn Glu Asp Leu Phe Val Cys Glu Tyr Gln Gly Gln Ser Ser
            195                 200                 205

Asp Leu Pro Gln Pro Pro Val Asn Ala Gly Gly Ser Gly Gly Gly
    210                 215                 220

Ser Gly Gly Gly Ser Glu Gly Gly Ser Glu Gly Gly Ser Glu
225                 230                 235                 240

Gly Gly Gly Ser Glu Gly Gly Ser Gly Gly Ser Gly Ser Gly
            245                 250                 255

Asp Phe Asp Tyr Glu Lys Met Ala Ala Asn Lys Gly Ala Met Thr
            260                 265                 270

Glu Asn Ala Asp Glu Asn Ala Leu Gln Ser Asp Ala Lys Gly Lys Leu
            275                 280                 285

Asp Ser Val Ala Thr Asp Tyr Gly Ala Ala Ile Asp Gly Phe Ile Gly
    290                 295                 300

Asp Val Ser Gly Leu Ala Asn Gly Asn Gly Ala Thr Gly Asp Phe Ala
305                 310                 315                 320

Gly Ser Asn Ser Gln Met Ala Gln Val Gly Asp Gly Asp Asn Ser Pro
            325                 330                 335

Leu Met Asn Asn Phe Arg Gln Tyr Leu Pro Ser Leu Pro Gln Ser Val
            340                 345                 350

Glu Cys Arg Pro Phe Val Phe Gly Ala Gly Lys Pro Tyr Glu Phe Ser
            355                 360                 365

Ile Asp Cys Asp Lys Ile Asn Leu Phe Arg Gly Val Phe Ala Phe Leu
    370                 375                 380

Leu Tyr Val Ala Thr Phe Met Tyr Val Phe Ser Thr Phe Ala Asn Ile
385                 390                 395                 400

Leu Arg Asn Lys Glu Ser
            405

<210> SEQ ID NO 2
<211> LENGTH: 406
<212> TYPE: PRT
<213> ORGANISM: Artificial sequence
<220> FEATURE:
<223> OTHER INFORMATION: Synthetic Construct

<400> SEQUENCE: 2

Ala Glu Thr Val Glu Ser Cys Pro Ala Lys Pro His Thr Glu Asn Ser
1               5                   10                  15

Phe Thr Asn Val Trp Lys Asp Asp Lys Thr Leu Asp Arg Tyr Ala Asn
            20                  25                  30

Tyr Glu Gly Cys Leu Trp Asn Ala Thr Gly Val Val Val Cys Thr Gly
        35                  40                  45

Asp Glu Thr Gln Cys Tyr Gly Thr Trp Val Pro Ile Gly Leu Ala Ile
    50                  55                  60

Pro Glu Asn Glu Gly Gly Ser Glu Gly Gly Ser Glu Gly Gly
65                  70                  75                  80

Gly Ser Glu Gly Gly Gly Thr Lys Pro Pro Glu Tyr Gly Asp Thr Pro
            85                  90                  95

Ile Pro Gly Tyr Thr Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
        115                 120                 125

Gln Pro Leu Asn Thr Phe Met Phe Gln Asn Asn Arg Phe Arg Asn Arg
    130                 135                 140
```

Gln Gly Ala Leu Thr Val Tyr Thr Gly Thr Val Thr Gln Gly Thr Asp
145                 150                 155                 160

Pro Val Lys Thr Tyr Tyr Gln Tyr Thr Pro Val Ser Ser Lys Ala Met
                165                 170                 175

Tyr Asp Ala Tyr Trp Asn Gly Lys Phe Arg Asp Cys Ala Phe His Ser
            180                 185                 190

Gly Phe Asn Glu Asp Leu Phe Val Cys Glu Tyr Gln Gly Gln Ser Ser
        195                 200                 205

Asp Leu Pro Gln Pro Val Asn Ala Gly Gly Ser Gly Gly Gly
    210                 215                 220

Ser Gly Gly Gly Ser Glu Gly Gly Ser Glu Gly Gly Ser Glu
225                 230                 235                 240

Gly Gly Gly Ser Glu Gly Gly Ser Gly Gly Ser Gly Ser Gly
                245                 250                 255

Asp Phe Asp Tyr Glu Lys Met Ala Asn Ala Asn Lys Gly Ala Met Thr
            260                 265                 270

Glu Asn Ala Asp Glu Asn Ala Leu Gln Ser Asp Ala Lys Gly Lys Leu
        275                 280                 285

Asp Ser Val Ala Thr Asp Tyr Gly Ala Ala Ile Asp Gly Phe Ile Gly
290                 295                 300

Asp Val Ser Gly Leu Ala Asn Gly Asn Gly Ala Thr Gly Asp Phe Ala
305                 310                 315                 320

Gly Ser Asn Ser Gln Met Ala Gln Val Gly Asp Gly Asp Asn Ser Pro
                325                 330                 335

Leu Met Asn Asn Phe Arg Gln Tyr Leu Pro Ser Leu Pro Gln Ser Val
            340                 345                 350

Glu Cys Arg Pro Phe Val Phe Gly Ala Gly Lys Pro Tyr Glu Phe Ser
        355                 360                 365

Ile Asp Cys Asp Lys Ile Asn Leu Phe Arg Gly Val Phe Ala Phe Leu
370                 375                 380

Leu Tyr Val Ala Thr Phe Met Tyr Val Phe Ser Thr Phe Ala Asn Ile
385                 390                 395                 400

Leu Arg Asn Lys Glu Ser
                405

<210> SEQ ID NO 3
<211> LENGTH: 1218
<212> TYPE: DNA
<213> ORGANISM: Artificial sequence
<220> FEATURE:
<223> OTHER INFORMATION: Synthetic Construct

<400> SEQUENCE: 3
gccgagacag tggagagctg cctggccaag tcgcacaccg agaacagctt caccaatgtt      60
tggaaggatg ataagaccct ggaccgctat gccaattacg aaggttgctt atggaacgca     120
accggtgtgg ttgtgtgcac aggcgatgag acccaatgct atggcacctg ggtgccgatc     180
ggtctggcaa ttccggagaa cgaaggcgga ggtagcgaag gaggtggaag tgaaggcgga     240
ggatcggaag ggggtggcac aaagccacca gaatatggag acaccccgat tccaggttac     300
acctacatta tccgctggga tggtacatac cctccaggca ccgaacagaa tccggcaaac     360
ccgaacccga gcctggaaga agccaaccg ctgaacacat ttatgttcca aaacaaccgt     420
tttcgtaacc gtcaaggagc cctgaccgta taccccggta cagtgaccca gggtacagat     480
ccggtgaaga cctactatca atatacaccg gttagcagca aggcaatgta cgatgcatat     540

```
tggaatggca agtttcgtga ttgtgcattt catagcggtt tcaacgaaga cctgtttgtg      600
tgcgaatacc agggtcagag cagcgattta ccgcagccac cggttaacgc aggtggtgga      660
agcggagggg gaagtggcgg tgggtcagaa ggcggaggat cggaaggagg tgggagtgaa      720
ggagggggaa gcgaaggagg gggatcagga ggtggtagcg gaagtggcga cttcgactac      780
gagaagatgg ccaatgcaaa caaaggcgca atgacagaga acgcagacga gaatgcactg      840
caaagtgatg caaagggtaa gctggacagc gttgcaaccg actatggagc agcaattgac      900
ggctttatcg agatgtcag cggtctggcg aacggcaacg agcaacagg cgacttcgca        960 ggtagcaaca gccagatggc acaggttgga gatggcgaca cagtccgct gatgaacaac       1020 tttcgccagt acctgccgag tctgccacaa agcgtcgagt gccgtccgtt tgttttcggt      1080
gcaggcaagc cgtacgagtt cagcatcgac tgcgataaga ttaatctttt tcgcggagtt      1140
ttcgcattcc tgctgtacgt ggcaacgttc atgtacgttt cagcacctt cgccaatatc       1200 ttacgcaaca aagaaagc                                                    1218

<210> SEQ ID NO 4
<211> LENGTH: 1218
<212> TYPE: DNA
<213> ORGANISM: Artificial sequence
<220> FEATURE:
<223> OTHER INFORMATION: Synthetic Construct

<400> SEQUENCE: 4
gccgaaactg ttgaaagttg tccggcaaaa ccccatacag aaaattcatt tactaacgtc       60
tggaaagacg acaaaacttt agatcgttac gctaactatg agggctgtct gtggaatgct      120
acaggcgttg tagtttgtac tggtgacgaa actcagtgtt acggtacatg ggttcctatt      180
gggcttgcta tccctgaaaa tgagggtggt ggctctgagg gtggcggttc tgagggtggc      240
ggttctgagg gtggcggtac taaacctcct gagtacggtg atacacctat tccgggctat      300
acttatatca accctctcga cggcacttat ccgcctggta ctgagcaaaa ccccgctaat      360
cctaatcctt ctcttgagga gtctcagcct cttaatactt tcatgtttca gaataatagg      420
ttccgaaata ggcaggggc attaactgtt tatacgggca ctgttactca aggcactgac       480
cccgttaaaa cttattacca gtacactcct gtatcatcaa aagccatgta tgacgcttac      540
tggaacggta aattcagaga ctgcgctttc cattctggct ttaatgagga tttatttgtt      600
tgtgaatatc aaggccaatc gtctgacctg cctcaacctc ctgtcaatgc tggcggcggc      660
tctggtggtg gttctggtgg cggctctgag ggtggtggct ctgagggtgg cggttctgag      720
ggtggcggct ctgagggagg cggttccggt ggtggctctg gttccggtga ttttgattat      780
gaaaagatgg caaacgctaa taggggggct atgaccgaaa atgccgatga aaacgcgcta      840
cagtctgacg ctaaaggcaa acttgattct gtcgctactg attacggtgc tgctatcgat      900
ggtttcattg gtgacgtttc cggccttgct aatggtaatg gtgctactgg tgattttgct      960
ggctctaatt cccaaatggc tcaagtcggt gacggtgata attcaccttt aatgaataat      1020
ttccgtcaat atttaccttc cctccctcaa tcggttgaat gtcgcccttt tgtctttggc      1080
gctggtaaac catatgaatt ttctattgat tgtgacaaaa taaacttatt ccgtggtgtc      1140
tttgcgtttc ttttatatgt tgccaccttt atgtatgtat ttctacgttt tgctaacata      1200
ctgcgtaata aggagtct                                                    1218
```

<210> SEQ ID NO 5
<211> LENGTH: 1218
<212> TYPE: DNA
<213> ORGANISM: Artificial sequence
<220> FEATURE:
<223> OTHER INFORMATION: Synthetic Construct

<400> SEQUENCE: 5

| | | | | | |
|---|---|---|---|---|---|
| gccgaaactg | ttgaaagttg | tttagcaaaa | tcccatacag | aaaattcatt | tactaacgtc | 60 |
| tggaaagacg | acaaaacttt | agatcgttac | gctaactatg | agggctgtct | gtggaatgct | 120 |
| acaggcgttg | tagtttgtac | tggtgacgaa | actcagtgtt | acggtacatg | ggttcctatt | 180 |
| gggcttgcta | tccctgaaaa | tgagggtggt | ggctctgagg | tggcggttc | tgagggtggc | 240 |
| ggttctgagg | gtggcggtac | taaacctcct | gagtacggtg | atacacctat | tccgggctat | 300 |
| acttatatca | accctctcga | cggcacttat | ccgcctggta | ctgagcaaaa | ccccgctaat | 360 |
| cctaatcctt | ctcttgagga | gtctcagcct | cttaatactt | tcatgtttca | gaataatagg | 420 |
| ttccgaaata | ggcagggggc | attaactgtt | tatacgggca | ctgttactca | aggcactgac | 480 |
| cccgttaaaa | cttattacca | gtacactcct | gtatcatcaa | aagccatgta | tgacgcttac | 540 |
| tggaacggta | aattcagaga | ctgcgctttc | cattctggct | ttaatgagga | tttatttgtt | 600 |
| tgtgaatatc | aaggccaatc | gtctgacctg | cctcaacctc | ctgtcaatgc | tggcggcggc | 660 |
| tctggtggtg | gttctggtgg | cggctctgag | ggtggtggct | ctgagggtgg | cggttctgag | 720 |
| ggtggcggct | ctgagggagg | cggttccggt | ggtggctctg | gttccggtga | ttttgattat | 780 |
| gaaaagatgg | caaacgctaa | taagggggct | atgaccgaaa | atgccgatga | aaacgcgcta | 840 |
| cagtctgacg | ctaaaggcaa | acttgattct | gtcgctactg | attacggtgc | tgctatcgat | 900 |
| ggtttcattg | gtgacgtttc | cggccttgct | aatggtaatg | gtgctactgg | tgattttgct | 960 |
| ggctctaatt | cccaaatggc | tcaagtcggt | gacggtgata | attcaccttt | aatgaataat | 1020 |
| ttccgtcaat | atttaccttc | cctccctcaa | tcggttgaat | gtcgcccttt | tgtctttggc | 1080 |
| gctggtaaac | catatgaatt | ttctattgat | tgtgacaaaa | taaacttatt | ccgtggtgtc | 1140 |
| tttgcgtttc | ttttatatgt | tgccaccttt | atgtatgtat | tttctacgtt | tgctaacata | 1200 |
| ctgcgtaata | aggagtct | | | | | 1218 |

<210> SEQ ID NO 6
<211> LENGTH: 8422
<212> TYPE: DNA
<213> ORGANISM: Artificial sequence
<220> FEATURE:
<223> OTHER INFORMATION: Synthetic Construct

<400> SEQUENCE: 6

| | | | | | |
|---|---|---|---|---|---|
| aatgctacta | ctattagtag | aattgatgcc | accttttcag | ctcgcgcccc | aaatgaaaat | 60 |
| atagctaaac | aggttattga | ccatttgcga | aatgtatcta | atggtcaaac | taaatctact | 120 |
| cgttcgcaga | attgggaatc | aactgttata | tggaatgaaa | cttccagaca | ccgtacttta | 180 |
| gttgcatatt | taaaacatgt | tgagctacag | cattatattc | agcaattaag | ctctaagcca | 240 |
| tctgcaaaaa | tgacctctta | tcaaaaggag | caattaaagg | tactctctaa | tcctgacctg | 300 |
| ttggagtttg | cttccggtct | ggttcgcttt | gaagctcgaa | ttaaaacgcg | atatttgaag | 360 |
| tctttcgggc | ttcctcttaa | tctttttgat | gcaatccgct | ttgcttctga | ctataatagt | 420 |
| cagggtaaag | acctgatttt | tgatttatgg | tcattctcgt | tttctgaact | gtttaaagca | 480 |
| tttgaggggg | attcaatgaa | tatttatgac | gattccgcag | tattggacgc | tatccagtct | 540 |

```
aaacatttta ctgttacccc ctctggcaaa acttcttttg caaaagcctc tcgctatttt      600
ggtttttatc gtcgtctggt aaacgagggt tatgatagtg ttgctcttac tatgcctcgt      660 aattccttt ggcgttatgt atctgcatta gttgaatgtg gtattcctaa atctcaactg       720
atgaatcttt ctacctgtaa taatgttgtt ccgttagttc gttttattaa cgtagatttt     780
tcttcccaac gtcctgactg gtataatgag ccagttctta aaatcgcata aggtaattca      840
caatgattaa agttgaaatt aaaccatctc aagcccaatt tactactcgt tctggtgttt      900
ctcgtcaggg caagccttat tcactgaatg agcagctttg ttacgttgat ttgggtaatg      960
aatatccggt tcttgtcaag attactcttg atgaaggtca gccagcctat gcgcctggtc     1020
tgtacaccgt tcatctgtcc tctttcaaag ttggtcagtt cggttccctt atgattgacc     1080
gtctgcgcct cgttccggct aagtaacatg gagcaggtcg cggatttcga cacaatttat     1140
caggcgatga tacaaatctc cgttgtactt tgtttcgcgc ttggtataat cgctgggggt     1200
caaagatgag tgttttagtg tattcttttg cctctttcgt tttaggttgg tgccttcgta     1260
gtggcattac gtatttacc cgtttaatgg aaacttcctc atgaaaaagt ctttagtcct     1320
caaagcctct gtagccgttg ctaccctcgt tccgatgctg tctttcgctg ctgagggtga     1380
cgatcccgca aaagcggcct ttaactccct gcaagcctca gcgaccgaat atatcggtta     1440
tgcgtgggcg atggttgttg tcattgtcgg cgcaactatc ggtatcaagc tgtttaagaa     1500
attcacctcg aaagcaagct gataaaccga tacaattaaa ggctcctttt ggagcctttt     1560
ttttggagat tttcaacgtg aaaaaattat tattcgcaat tcctttagtt gttcctttct     1620
attctcactc cgccgaaact gttgaaagtt gtttagcaaa atcccataca gaaaattcat     1680
ttactaacgt ctggaaagac gacaaaactt tagatcgtta cgctaactat gagggctgtc     1740
tgtggaatgc tacaggcgtt gtagtttgta ctggtgacga aactcagtgt tacggtacat     1800
gggttcctat tgggcttgct atccctgaaa atgagggtgg tggctctgag ggtggcggtt     1860
ctgagggtgg cggttctgag ggtggcggta ctaaacctcc tgagtacggt gatacaccta     1920
ttccgggcta tacttatatc aaccctctcg acggcactta tccgcctggt actgagcaaa     1980
accccgctaa tcctaatcct tctcttgagg agtctcagcc tcttaatact ttcatgtttc     2040
agaataatag gttccgaaat aggcaggggg cattaactgt ttatacgggc actgttactc     2100
aaggcactga ccccgttaaa acttattacc agtacactcc tgtatcatca aaagccatgt     2160
atgacgctta ctggaacggt aaattcagag actgcgcttt ccattctggc tttaatgagg     2220
atttatttgt ttgtgaatat caaggccaat cgtctgacct gcctcaacct cctgtcaatg     2280
ctggcggcgg ctctggtggt ggttctggtg gcggctctga gggtggtggc tctgagggtg     2340
gcggttctga gggtggcggc tctgaggag gcggttccgg tggtggctct ggttccggtg     2400
attttgatta tgaaagatg gcaaacgcta ataagggggc tatgaccgaa atgccgatg      2460 aaaacgcgct acagtctgac gctaaaggca aacttgattc tgtcgctact gattacggtg     2520
ctgctatcga tggtttcatt ggtgacgttt ccggccttgc taatggtaat ggtgctactg     2580
gtgattttgc tggctctaat tcccaaatgg ctcaagtcgg tgacggtgat aattcacctt     2640
taatgaataa tttccgtcaa tatttacctt ccctccctca atcggttgaa tgtcgccctt     2700
ttgtctttgg cgctggtaaa ccatatgaat tttctattga ttgtgacaaa ataaacttat     2760
tccgtggtgt ctttgcgttt cttttatatg ttgccacctt tatgtatgta ttttctacgt     2820
ttgctaacat actgcgtaat aaggagtctt aatcatgcca gttcttttgg gtattccgtt     2880
attattgcgt ttcctcggtt tccttctggt aactttgttc ggctatctgc ttacttttct     2940
```

-continued

```
taaaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt cattttttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttttctagt aattatgatt    3840 ccggtgttta ttcttatttta acgccttatt tatcacacgg tcggtatttc aaaccattaa    3900
atttaggtca gaagatgaag cttactaaaa tatatttgaa aaagttttca cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaatgattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta agatattttt agataacctt cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta tttttaatgg cgatgtttta    4980
gggctatcag ttcgcgcatt aaagactaat agccattcaa aaatattgtc tgtgccacgt    5040
attcttacgc tttcaggtca gaagggttct atctctgttg gccagaatgt ccctttattt    5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
```

```
ggtggcctca ctgattataa aaacacttct caggattctg gcgtaccgtt cctgtctaaa   5400
atccctttaa tcggcctcct gtttagctcc cgctctgatt ctaacgagga aagcacgtta   5460
tacgtgctcg tcaaagcaac catagtacgc gccctgtagc ggcgcattaa gcgcggcggg   5520
tgtggtggtt acgcgcagcg tgaccgctac acttgccagc gccctagcgc ccgctccttt   5580
cgctttcttc ccttcctttc tcgccacgtt cgccggcttt ccccgtcaag ctctaaatcg   5640
ggggctccct ttagggttcc gatttagtgc tttacggcac ctcgacccca aaaaacttga   5700
tttgggtgat ggttcacgta gtgggccatc gccctgatag acggtttttc gccctttgac   5760
gttggagtcc acgttcttta atagtggact cttgttccaa actggaacaa cactcaaccc   5820
tatctcgggc tattcttttg atttataagg gattttgccg atttcggaac caccatcaca   5880
caggattttc gcctgctggg gcaaaccagc gtggaccgct tgctgcaact ctctcagggc   5940
caggcggtga agggcaatca gctgttgccc gtctcgctgg tgaaaagaaa aaccaccctg   6000
gcgcccaata cgcaaaccgc ctctccccgc gcgttggccg attcattaat gcagctggca   6060
cgacaggttt cccgactgga aagcgggcag tgagcgcaac gcaattaatg tgagttagct   6120
cactcattag gcaccccagg cttgacactt tatgcttccg gctcgtataa tgtgtggaat   6180
tgtgagcgga taacaatttc acacgccaag agacagtca taatgaaata cctattgcct   6240
acggcagccg ctggattgtt attactcgct gcccaaccag ccatggccgg cggaggatct   6300
ggcgagcaaa agctcattag tgaagaggat cttgccgaga cagtggagag ctgcctggcc   6360
aagtcgcaca ccgagaacag cttcaccaat gtttggaagg atgataagac cctggaccgc   6420
tatgccaatt acgaaggttg cttatggaac gcaaccggtg tggttgtgtg cacaggcgat   6480
gagacccaat gctatggcac ctgggtgccg atcggtctgg caattccgga gaacgaaggc   6540
ggaggtagcg aaggaggtgg aagtgaaggc ggaggatcgg aaggggggtgg cacaaagcca   6600
ccagaatatg gagacacccc gattccaggt tacacctaca ttaatccgct ggatggtaca   6660
taccctccag gcaccgaaca gaatccggca aacccgaacc cgagcctgga gaaaagccaa   6720
ccgctgaaca catttatgtt ccaaaacaac cgttttcgta accgtcaagg agccctgacc   6780
gtatacaccg gtacagtgac ccagggtaca gatccggtga agacctacta tcaatataca   6840
ccggttagca gcaaggcaat gtacgatgca tattggaatg gcaagtttcg tgattgtgca   6900
tttcatagcg gtttcaacga agacctgttt gtgtgcgaat accagggtca gagcagcgat   6960
ttaccgcagc caccggttaa cgcaggtggt ggaagcggag ggggaagtgg cggtgggtca   7020
gaaggcggag gatcggaagg aggtgggagt gaaggagggg gaagcgaagg aggggggatca   7080
ggaggtggta gcggaagtgg cgacttcgac tacgagaaga tggccaatgc aaacaaaggc   7140
gcaatgacag agaacgcaga cgagaatgca ctgcaaagtg atgcaaaggg taagctggac   7200
agcgttgcaa ccgactatgg agcagcaatt gacggcttta tcggagatgt cagcggtctg   7260
gcgaacggca acggagcaac aggcgacttc gcaggtagca acagccagat ggcacaggtt   7320
ggagatggcg acaacagtcc gctgatgaac aactttcgcc agtacctgcc gagtctgcca   7380
caaagcgtcg agtgccgtcc gtttgttttc ggtgcaggca gccgtacga gttcagcatc   7440
gactgcgata gattaatct ttttcgcgga gttttcgcat tcctgctgta cgtggcaacg   7500
ttcatgtacg ttttcagcac cttcgccaat atcttacgca acaaagaaag ctaagcaata   7560
gcgaagaggc ccgcaccgat cgcccttccc aacagttgcg cagcctgaat ggcgaatggc   7620
gctttgcctg gtttccggca ccagaagcgg tgccggaaag ctggctggag tgcgatcttc   7680
ctgaggccga tactgtcgtc gtcccctcaa actggcagat gcacggttac gatgcgccca   7740
```

-continued

```
tctacaccaa cgtgacctat cccattacgg tcaatccgcc gtttgttccc acggagaatc      7800
cgacgggttg ttactcgctc acatttaatg ttgatgaaag ctggctacag gaaggccaga      7860
cgcgaattat ttttgatggc gttcctattg gttaaaaaat gagctgattt aacaaaaatt      7920
taatgcgaat tttaacaaaa tattaacgtt tacaatttaa atatttgctt atacaatctt      7980 cctgttttg gggcttttct gattatcaac cggggtacat atgattgaca tgctagtttt       8040
acgattaccg ttcatcgatt ctcttgtttg ctccagactc tcaggcaatg acctgatagc      8100
ctttgtagat ctctcaaaaa tagctaccct ctccggcatt aatttatcag ctagaacggt      8160
tgaatatcat attgatggtg atttgactgt ctccggcctt tctcacccct ttgaatcttt      8220
acctacacat tactcaggca ttgcatttaa aatatatgag ggttctaaaa atttttatcc      8280
ttgcgttgaa ataaaggctt ctcccgcaaa agtattacag ggtcataatg ttttttggtac     8340 aaccgattta gctttatgct ctgaggcttt attgcttaat tttgctaatt ctttgccttg      8400
cctgtatgat ttattggacg tt                                               8422
```

```
<210> SEQ ID NO 7
<211> LENGTH: 10
<212> TYPE: PRT
<213> ORGANISM: Artificial sequence
<220> FEATURE:
<223> OTHER INFORMATION: Synthetic Construct

<400> SEQUENCE: 7

Glu Gln Lys Leu Ile Ser Glu Glu Asp Leu
1               5                   10

<210> SEQ ID NO 8
<211> LENGTH: 30
<212> TYPE: DNA
<213> ORGANISM: Artificial sequence
<220> FEATURE:
<223> OTHER INFORMATION: Synthetic Construct

<400> SEQUENCE: 8
gagcaaaagc tcattagtga agaggatctt                                       30

<210> SEQ ID NO 9
<211> LENGTH: 20
<212> TYPE: PRT
<213> ORGANISM: Artificial sequence
<220> FEATURE:
<223> OTHER INFORMATION: Synthetic Construct

<400> SEQUENCE: 9

Arg Thr Phe Cys Lys Glu Phe Gly Arg Tyr Val Ala Asp Glu Thr Tyr
1               5                   10                  15

Cys Ala Ala Leu
            20

<210> SEQ ID NO 10
<211> LENGTH: 60
<212> TYPE: DNA
<213> ORGANISM: Artificial sequence
<220> FEATURE:
<223> OTHER INFORMATION: Synthetic Construct

<400> SEQUENCE: 10 aggactttttt gtaaggagtt tgggcggtat gttgcggatg agacgtattg tgctgcgctt    60
```

<210> SEQ ID NO 11
<211> LENGTH: 20
<212> TYPE: PRT
<213> ORGANISM: Artificial sequence
<220> FEATURE:
<223> OTHER INFORMATION: Synthetic Construct

<400> SEQUENCE: 11

Ile Ser Leu Cys Asp Gln Pro Tyr Val Lys Ser Leu Asn Leu Pro Leu
1               5                   10                  15

Cys Pro Leu Ala
            20

<210> SEQ ID NO 12
<211> LENGTH: 60
<212> TYPE: DNA
<213> ORGANISM: Artificial sequence
<220> FEATURE:
<223> OTHER INFORMATION: Synthetic Construct

<400> SEQUENCE: 12
atttctttgt gtgatcagcc gtatgttaag agtcttaatc ttccgttgtg tccgcttgct    60

<210> SEQ ID NO 13
<211> LENGTH: 20
<212> TYPE: PRT
<213> ORGANISM: Artificial sequence
<220> FEATURE:
<223> OTHER INFORMATION: Synthetic Construct

<400> SEQUENCE: 13

Pro Pro Leu Cys Ser Trp Pro Ala Tyr Gln Lys Phe Gly Gly Pro Leu
1               5                   10                  15

Cys Thr Leu Gly
            20

<210> SEQ ID NO 14
<211> LENGTH: 60
<212> TYPE: DNA
<213> ORGANISM: Artificial sequence
<220> FEATURE:
<223> OTHER INFORMATION: Synthetic Construct

<400> SEQUENCE: 14
cctccgctgt gttcttggcc tgcttatcag aagtttggtg gtccgctgtg tacgcttggt    60

<210> SEQ ID NO 15
<211> LENGTH: 8422
<212> TYPE: DNA
<213> ORGANISM: Artificial sequence
<220> FEATURE:
<223> OTHER INFORMATION: Synthetic Construct

<400> SEQUENCE: 15
aatgctacta ctattagtag aattgatgcc accttttcag ctcgcgcccc aaatgaaaat    60
atagctaaac aggttattga ccatttgcga aatgtatcta atggtcaaac taaatctact   120
cgttcgcaga attgggaatc aactgttata tggaatgaaa cttccagaca ccgtacttta   180
gttgcatatt taaaacatgt tgagctacag cattatattc agcaattaag ctctaagcca   240
tctgcaaaaa tgacctctta tcaaaaggag caattaaagg tactctctaa tcctgacctg   300
ttggagtttg cttccggtct ggttcgcttt gaagctcgaa ttaaaacgcg atatttgaag   360
tctttcgggc ttcctcttaa tctttttgat gcaatccgct ttgcttctga ctataatagt   420

-continued

| | |
|---|---|
| cagggtaaag acctgatttt tgatttatgg tcattctcgt tttctgaact gtttaaagca | 480 |
| tttgaggggg attcaatgaa tatttatgac gattccgcag tattggacgc tatccagtct | 540 |
| aaacatttta ctgttacccc ctctggcaaa acttcttttg caaaagcctc tcgctatttt | 600 |
| ggttttatc gtcgtctggt aaacgagggt tatgatagtg ttgctcttac tatgcctcgt | 660 |
| aattccttt ggcgttatgt atctgcatta gttgaatgtg gtattcctaa atctcaactg | 720 |
| atgaatcttt ctacctgtaa taatgttgtt ccgttagttc gttttattaa cgtagatttt | 780 |
| tcttcccaac gtcctgactg gtataatgag ccagttctta aaatcgcata aggtaattca | 840 |
| caatgattaa agttgaaatt aaaccatctc aagcccaatt tactactcgt tctggtgttt | 900 |
| ctcgtcaggg caagccttat tcactgaatg agcagctttg ttacgttgat ttgggtaatg | 960 |
| aatatccggt tcttgtcaag attactcttg atgaaggtca gccagcctat gcgcctggtc | 1020 |
| tgtacaccgt tcatctgtcc tctttcaaag ttggtcagtt cggttccctt atgattgacc | 1080 |
| gtctgcgcct cgttccggct aagtaacatg gagcaggtcg cggatttcga cacaatttat | 1140 |
| caggcgatga tacaaatctc cgttgtactt tgtttcgcgc ttggtataat cgctgggggt | 1200 |
| caaagatgag tgttttagtg tattcttttg cctctttcgt tttaggttgg tgccttcgta | 1260 |
| gtggcattac gtattttacc cgtttaatgg aaacttcctc atgaaaaagt ctttagtcct | 1320 |
| caaagcctct gtagccgttg ctaccctcgt tccgatgctg tctttcgctg ctgagggtga | 1380 |
| cgatcccgca aaagcggcct ttaactccct gcaagcctca gcgaccgaat atatcggtta | 1440 |
| tgcgtgggcg atggttgttg tcattgtcgg cgcaactatc ggtatcaagc tgtttaagaa | 1500 |
| attcacctcg aaagcaagct gataaaccga tacaattaaa ggctccttt ggagcctttt | 1560 |
| ttttggagat tttcaacgtg aaaaaattat tattcgcaat tcctttagtt gttcctttct | 1620 |
| attctcactc cgccgaaact gttgaaagtt gtccggcaaa accccataca gaaaattcat | 1680 |
| ttactaacgt ctggaaagac gacaaaactt tagatcgtta cgctaactat gagggctgtc | 1740 |
| tgtggaatgc tacaggcgtt gtagtttgta ctggtgacga aactcagtgt tacggtacat | 1800 |
| gggttcctat tgggcttgct atccctgaaa atgagggtgg tggctctgag ggtggcggtt | 1860 |
| ctgagggtgg cggttctgag ggtggcggta ctaaacctcc tgagtacggt gatacaccta | 1920 |
| ttccgggcta tacttatatc aaccctctcg acggcactta tccgcctggt actgagcaaa | 1980 |
| accccgctaa tcctaatcct tctcttgagg agtctcagcc tcttaatact ttcatgtttc | 2040 |
| agaataatag gttccgaaat aggcaggggg cattaactgt ttatacgggc actgttactc | 2100 |
| aaggcactga ccccgttaaa acttattacc agtacactcc tgtatcatca aaagccatgt | 2160 |
| atgacgctta ctggaacggt aaattcagag actgcgcttt ccattctggc tttaatgagg | 2220 |
| atttatttgt ttgtgaatat caaggccaat cgtctgacct gcctcaacct cctgtcaatg | 2280 |
| ctggcggcgg ctctggtggt ggttctggtg gcggctctga gggtggtggc tctgagggtg | 2340 |
| gcggttctga gggtggcggc tctgagggag gcggttccgg tggtggctct ggttccggtg | 2400 |
| attttgatta tgaaaagatg gcaaacgcta ataagggggc tatgaccgaa aatgccgatg | 2460 |
| aaaacgcgct acagtctgac gctaaaggca aacttgattc tgtcgctact gattacggtg | 2520 |
| ctgctatcga tggtttcatt ggtgacgttt ccggccttgc taatggtaat ggtgctactg | 2580 |
| gtgattttgc tggctctaat tcccaaatgg ctcaagtcgg tgacggtgat aattcacctt | 2640 |
| taatgaataa tttccgtcaa tatttacctt ccctccctca atcggttgaa tgtcgccctt | 2700 |
| ttgtctttgg cgctggtaaa ccatatgaat tttctattga ttgtgacaaa ataaacttat | 2760 |
| tccgtggtgt cttttgcgttt cttttatatg ttgccacctt tatgtatgta ttttctacgt | 2820 |

```
ttgctaacat actgcgtaat aaggagtctt aatcatgcca gttctttttgg gtattccgtt    2880
attattgcgt ttcctcggtt tccttctggt aactttgttc ggctatctgc ttacttttct    2940
taaaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttccttgttc aggacttatc tattgttgat aaacaggcgc    3600
gttctgcatt agctgaacat gttgtttatt gtcgtcgtct ggacagaatt acttttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttttctagt aattatgatt    3840
ccggtgttta ttcttatttta acgccttatt tatcacacgg tcggtatttc aaaccattaa    3900
atttaggtca gaagatgaag cttactaaaa tatatttgaa aaagttttca cgcgttcttt    3960
gtcttgcgat tggatttgca tcagcattta catatagtta tataacccaa cctaagccgg    4020
aggttaaaaa ggtagtctct cagacctatg atttttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttctttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaatgattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta agatatttt agataaccttt cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta tttttaatgg cgatgtttta    4980
gggctatcag ttcgcgcatt aaagactaat agccattcaa aaatattgtc tgtgccacgt    5040
attcttacgc tttcaggtca gaagggttct atctctgttg gccagaatgt ccctttttatt    5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
```

```
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg gcgtaccgtt cctgtctaaa    5400 atcccttttaa tcggcctcct gtttagctcc cgctctgatt ctaacgagga agcacgttta   5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggtttttc gccctttgac    5760
gttggagtcc acgttcttta atagtggact cttgttccaa actggaacaa cactcaaccc    5820
tatctcgggc tattcttttg atttataagg gattttgccg atttcggaac caccatcaca    5880
caggattttc gcctgctggg gcaaaccagc gtggaccgct tgctgcaact ctctcagggc    5940
caggcggtga agggcaatca gctgttgccc gtctcgctgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg cttgacactt tatgcttccg gctcgtataa tgtgtggaat    6180
tgtgagcgga taacaatttc acacgccaag agacagtcaa taatgaaata cctattgcct    6240
acggcagccg ctggattgtt attactcgct gcccaaccag ccatggccgg cggaggatct    6300
ggcgagcaaa agctcattag tgaagaggat cttgccgaga cagtgagag ctgcctggcc     6360 aagtcgcaca ccgagaacag cttcaccaat gtttggaagg atgataagac cctggaccgc    6420
tatgccaatt acgaaggttg cttatggaac gcaaccggtg tggttgtgtg cacaggcgat    6480
gagacccaat gctatggcac ctgggtgccg atcggtctgg caattccgga gaacgaaggc    6540
ggaggtagcg aaggaggtgg aagtgaaggc ggaggatcgg aagggggtgg cacaaagcca    6600
ccagaatatg gagacacccc gattccaggt tacacctaca ttaatccgct ggatggtaca    6660
taccctccag gcaccgaaca gaatccggca aacccgaacc cgagcctgga agaaagccaa    6720
ccgctgaaca catttatgtt ccaaaacaac cgttttcgta accgtcaagg agccctgacc    6780
gtatacaccg gtacagtgac ccagggtaca gatccggtga agacctacta tcaatataca    6840
ccggttagca gcaaggcaat gtacgatgca tattggaatg gcaagtttcg tgattgtgca    6900
tttcatagcg gtttcaacga agacctgttt gtgtgcgaat accagggtca gagcagcgat    6960
ttaccgcagc caccggttaa cgcaggtggt ggaagcggag ggggaagtgg cggtgggtca    7020
gaaggcggag gatcggaagg aggtgggagt gaaggagggg gaagcgaagg aggggggatca   7080 ggaggtggta gcggaagtgg cgacttcgac tacgagaaga tggccaatgc aaacaaaggc    7140
gcaatgacag agaacgcaga cgagaatgca ctgcaaagtg atgcaaaggg taagctggac    7200
agcgttgcaa ccgactatgg agcagcaatt gacggcttta tcggagatgt cagcggtctg    7260
gcgaacggca acggagcaac aggcgacttc gcaggtagca acagccagat ggcacaggtt    7320
ggagatggca caacagtcc gctgatgaac aactttcgcc agtacctgcc gagtctgcca    7380
caaagcgtcg agtgccgtcc gtttgttttc ggtgcaggca gccgtacga gttcagcatc    7440 gactgcgata agattaatct ttttcgcgga gttttcgcat tcctgctgta cgtggcaacg    7500
ttcatgtacg ttttcagcac cttcgccaat atcttacgaa acaaagaaag ctaagcaata    7560
gcgaagaggc ccgcaccgat cgcccttccc aacagttgcg cagcctgaat ggcgaatggc    7620
```

| | |
|---|---|
| gctttgcctg gtttccggca ccagaagcgg tgccggaaag ctggctggag tgcgatcttc | 7680 |
| ctgaggccga tactgtcgtc gtcccctcaa actggcagat gcacggttac gatgcgccca | 7740 |
| tctacaccaa cgtgacctat cccattacgg tcaatccgcc gtttgttccc acggagaatc | 7800 |
| cgacgggttg ttactcgctc acatttaatg ttgatgaaag ctggctacag gaaggccaga | 7860 |
| cgcgaattat ttttgatggc gttcctattg gttaaaaaat gagctgattt aacaaaaatt | 7920 |
| taatgcgaat tttaacaaaa tattaacgtt tacaatttaa atatttgctt atacaatctt | 7980 |
| cctgtttttg ggcttttct gattatcaac cggggtacat atgattgaca tgctagtttt | 8040 |
| acgattaccg ttcatcgatt ctcttgtttg ctccagactc tcaggcaatg acctgatagc | 8100 |
| ctttgtagat ctctcaaaaa tagctaccct ctccggcatt aatttatcag ctagaacggt | 8160 |
| tgaatatcat attgatggtg atttgactgt ctccggcctt tctcacccct ttgaatcttt | 8220 |
| acctacacat tactcaggca ttgcatttaa aatatatgag ggttctaaaa attttttatcc | 8280 |
| ttgcgttgaa ataaaggctt ctcccgcaaa agtattacag ggtcataatg ttttttggtac | 8340 |
| aaccgattta gctttatgct ctgaggcttt attgcttaat tttgctaatt ctttgccttg | 8400 |
| cctgtatgat ttattggacg tt | 8422 |

```
<210> SEQ ID NO 16
<211> LENGTH: 15
<212> TYPE: DNA
<213> ORGANISM: Artificial sequence
<220> FEATURE:
<223> OTHER INFORMATION: Synthetic Construct

<400> SEQUENCE: 16
ggcggaggat ctggc                                                15

<210> SEQ ID NO 17
<211> LENGTH: 54
<212> TYPE: DNA
<213> ORGANISM: Artificial sequence
<220> FEATURE:
<223> OTHER INFORMATION: Synthetic Construct

<400> SEQUENCE: 17
gtgaaaaaat tattattcgc aattccttta gttgttcctt tctattctca ctcc      54

<210> SEQ ID NO 18
<211> LENGTH: 18
<212> TYPE: PRT
<213> ORGANISM: Artificial sequence
<220> FEATURE:
<223> OTHER INFORMATION: Synthetic Construct

<400> SEQUENCE: 18

Val Lys Lys Leu Leu Phe Ala Ile Pro Leu Val Val Pro Phe Tyr Ser
1               5                   10                  15

His Ser

<210> SEQ ID NO 19
<211> LENGTH: 66
<212> TYPE: DNA
<213> ORGANISM: Artificial sequence
<220> FEATURE:
<223> OTHER INFORMATION: Synthetic Construct
```

-continued

<400> SEQUENCE: 19
atgaaatacc tattgcctac ggcagccgct ggattgttat tactcgctgc ccaaccagcc    60
atggcc    66

<210> SEQ ID NO 20
<211> LENGTH: 22
<212> TYPE: PRT
<213> ORGANISM: Artificial sequence
<220> FEATURE:
<223> OTHER INFORMATION: Synthetic Construct

<400> SEQUENCE: 20

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 21
<211> LENGTH: 406
<212> TYPE: PRT
<213> ORGANISM: Artificial sequence
<220> FEATURE:
<223> OTHER INFORMATION: Synthetic Construct

<400> SEQUENCE: 21

Ala Glu Thr Val Glu Ser Cys Pro Ala Lys Ser His Thr Glu Asn Ser
1               5                   10                  15

Phe Thr Asn Val Trp Lys Asp Asp Lys Thr Leu Asp Arg Tyr Ala Asn
            20                  25                  30

Tyr Glu Gly Cys Leu Trp Asn Ala Thr Gly Val Val Val Cys Thr Gly
        35                  40                  45

Asp Glu Thr Gln Cys Tyr Gly Thr Trp Val Pro Ile Gly Leu Ala Ile
    50                  55                  60

Pro Glu Asn Glu Gly Gly Ser Glu Gly Gly Ser Glu Gly Gly
65                  70                  75                  80

Gly Ser Glu Gly Gly Gly Thr Lys Pro Pro Glu Tyr Gly Asp Thr Pro
                85                  90                  95

Ile Pro Gly Tyr Thr Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
        115                 120                 125

Gln Pro Leu Asn Thr Phe Met Phe Gln Asn Asn Arg Phe Arg Asn Arg
    130                 135                 140

Gln Gly Ala Leu Thr Val Tyr Thr Gly Thr Val Thr Gln Gly Thr Asp
145                 150                 155                 160

Pro Val Lys Thr Tyr Tyr Gln Tyr Thr Pro Val Ser Ser Lys Ala Met
                165                 170                 175

Tyr Asp Ala Tyr Trp Asn Gly Lys Phe Arg Asp Cys Ala Phe His Ser
            180                 185                 190

Gly Phe Asn Glu Asp Leu Phe Val Cys Glu Tyr Gln Gly Gln Ser Ser
        195                 200                 205

Asp Leu Pro Gln Pro Pro Val Asn Ala Gly Gly Ser Gly Gly Gly Gly
    210                 215                 220

Ser Gly Gly Gly Ser Glu Gly Gly Ser Glu Gly Gly Ser Glu
225                 230                 235                 240

Gly Gly Gly Ser Glu Gly Gly Ser Gly Gly Ser Gly Ser Gly
                245                 250                 255

```
Asp Phe Asp Tyr Glu Lys Met Ala Asn Ala Asn Lys Gly Ala Met Thr
            260                 265                 270
Glu Asn Ala Asp Glu Asn Ala Leu Gln Ser Asp Ala Lys Gly Lys Leu
        275                 280                 285
Asp Ser Val Ala Thr Asp Tyr Gly Ala Ala Ile Asp Gly Phe Ile Gly
    290                 295                 300
Asp Val Ser Gly Leu Ala Asn Gly Asn Gly Ala Thr Gly Asp Phe Ala
305                 310                 315                 320
Gly Ser Asn Ser Gln Met Ala Gln Val Gly Asp Gly Asp Asn Ser Pro
                325                 330                 335
Leu Met Asn Asn Phe Arg Gln Tyr Leu Pro Ser Leu Pro Gln Ser Val
            340                 345                 350
Glu Cys Arg Pro Phe Val Phe Gly Ala Gly Lys Pro Tyr Glu Phe Ser
        355                 360                 365
Ile Asp Cys Asp Lys Ile Asn Leu Phe Arg Gly Val Phe Ala Phe Leu
    370                 375                 380
Leu Tyr Val Ala Thr Phe Met Tyr Val Phe Ser Thr Phe Ala Asn Ile
385                 390                 395                 400
Leu Arg Asn Lys Glu Ser
                405
```

<210> SEQ ID NO 22
<211> LENGTH: 406
<212> TYPE: PRT
<213> ORGANISM: Artificial sequence
<220> FEATURE:
<223> OTHER INFORMATION: Synthetic Construct

<400> SEQUENCE: 22

```
Ala Glu Thr Val Glu Ser Cys Leu Ala Lys Pro His Thr Glu Asn Ser
1               5                   10                  15
Phe Thr Asn Val Trp Lys Asp Asp Lys Thr Leu Asp Arg Tyr Ala Asn
            20                  25                  30
Tyr Glu Gly Cys Leu Trp Asn Ala Thr Gly Val Val Cys Thr Gly
        35                  40                  45
Asp Glu Thr Gln Cys Tyr Gly Thr Trp Val Pro Ile Gly Leu Ala Ile
    50                  55                  60
Pro Glu Asn Glu Gly Gly Ser Glu Gly Gly Ser Glu Gly Gly
65                  70                  75                  80
Gly Ser Glu Gly Gly Thr Lys Pro Pro Glu Tyr Gly Asp Thr Pro
                85                  90                  95
Ile Pro Gly Tyr Thr Tyr Ile Asn Pro Leu Asp Gly Thr Tyr Pro Pro
                100                 105                 110
Gly Thr Glu Gln Asn Pro Ala Asn Pro Asn Pro Ser Leu Glu Glu Ser
            115                 120                 125
Gln Pro Leu Asn Thr Phe Met Phe Gln Asn Asn Arg Phe Arg Asn Arg
        130                 135                 140
Gln Gly Ala Leu Thr Val Tyr Thr Gly Thr Val Thr Gln Gly Thr Asp
145                 150                 155                 160
Pro Val Lys Thr Tyr Tyr Gln Tyr Thr Pro Val Ser Ser Lys Ala Met
                165                 170                 175
Tyr Asp Ala Tyr Trp Asn Gly Lys Phe Arg Asp Cys Ala Phe His Ser
                180                 185                 190
Gly Phe Asn Glu Asp Leu Phe Val Cys Glu Tyr Gln Gly Gln Ser Ser
            195                 200                 205
```

```
Asp Leu Pro Gln Pro Pro Val Asn Ala Gly Gly Ser Gly Gly Gly
    210                 215                 220
Ser Gly Gly Gly Ser Glu Gly Gly Ser Glu Gly Gly Gly Ser Glu
225                 230                 235                 240
Gly Gly Gly Ser Glu Gly Gly Ser Gly Gly Ser Gly Ser Gly
                245                 250                 255
Asp Phe Asp Tyr Glu Lys Met Ala Asn Ala Asn Lys Gly Ala Met Thr
                260                 265                 270
Glu Asn Ala Asp Glu Asn Ala Leu Gln Ser Asp Ala Lys Gly Lys Leu
            275                 280                 285
Asp Ser Val Ala Thr Asp Tyr Gly Ala Ala Ile Asp Gly Phe Ile Gly
        290                 295                 300
Asp Val Ser Gly Leu Ala Asn Gly Asn Gly Ala Thr Gly Asp Phe Ala
305                 310                 315                 320
Gly Ser Asn Ser Gln Met Ala Gln Val Gly Asp Gly Asp Asn Ser Pro
                325                 330                 335
Leu Met Asn Asn Phe Arg Gln Tyr Leu Pro Ser Leu Pro Gln Ser Val
            340                 345                 350
Glu Cys Arg Pro Phe Val Phe Gly Ala Gly Lys Pro Tyr Glu Phe Ser
        355                 360                 365
Ile Asp Cys Asp Lys Ile Asn Leu Phe Arg Gly Val Phe Ala Phe Leu
370                 375                 380
Leu Tyr Val Ala Thr Phe Met Tyr Val Phe Ser Thr Phe Ala Asn Ile
385                 390                 395                 400

Leu Arg Asn Lys Glu Ser
                405

<210> SEQ ID NO 23
<211> LENGTH: 1218
<212> TYPE: DNA
<213> ORGANISM: Artificial sequence
<220> FEATURE:
<223> OTHER INFORMATION: Synthetic Construct

<400> SEQUENCE: 23
gccgaaactg ttgaaagttg tccggcaaaa tcccatacag aaaattcatt tactaacgtc      60 tggaagacg acaaaacttt agatcgttac gctaactatg agggctgtct gtggaatgct     120
acaggcgttg tagtttgtac tggtgacgaa actcagtgtt acggtacatg ggttcctatt     180
gggcttgcta tccctgaaaa tgagggtggt ggctctgagg gtggcggttc tgagggtggc     240
ggttctgagg gtggcggtac taaacctcct gagtacggtg atacacctat tccgggctat     300
acttatatca accctctcga cggcacttat ccgcctggta ctgagcaaaa ccccgctaat     360
cctaatcctt ctcttgagga gtctcagcct cttaatactt tcatgtttca gaataatagg     420
ttccgaaata ggcaggggc attaactgtt tatacgggca ctgttactca aggcactgac     480
cccgttaaaa cttattacca gtacactcct gtatcatcaa aagccatgta tgacgcttac     540
tggaacggta aattcagaga ctgcgctttc cattctggct ttaatgagga tttatttgtt     600
tgtgaatatc aaggccaatc gtctgacctg cctcaacctc ctgtcaatgc tggcggcggc     660
tctggtggtg gttctggtgg cggctctgag ggtggtggct ctgagggtgg cggttctgag     720
ggtggcggct ctgagggagg cggttccggt ggtggctctg gttccggtga ttttgattat     780
gaaaagatgg caaacgctaa taaggggct atgaccgaaa atgccgatga aaacgcgcta     840
cagtctgacg ctaaaggcaa acttgattct gtcgctactg attacggtgc tgctatcgat     900
```

| | |
|---|---|
| ggtttcattg gtgacgtttc cggccttgct aatggtaatg gtgctactgg tgattttgct | 960 |
| ggctctaatt cccaaatggc tcaagtcggt gacggtgata attcaccttt aatgaataat | 1020 |
| ttccgtcaat atttaccttc cctccctcaa tcggttgaat gtcgcccttt tgtctttggc | 1080 |
| gctggtaaac catatgaatt ttctattgat tgtgacaaaa taaacttatt ccgtggtgtc | 1140 |
| tttgcgtttc ttttatatgt tgccaccttt atgtatgtat tttctacgtt tgctaacata | 1200 |
| ctgcgtaata aggagtct | 1218 |

<210> SEQ ID NO 24
<211> LENGTH: 1218
<212> TYPE: DNA
<213> ORGANISM: Artificial sequence
<220> FEATURE:
<223> OTHER INFORMATION: Synthetic Construct

<400> SEQUENCE: 24

| | |
|---|---|
| gccgaaactg ttgaaagttg tttagcaaaa ccccatacag aaaattcatt tactaacgtc | 60 |
| tggaaagacg acaaaacttt agatcgttac gctaactatg agggctgtct gtggaatgct | 120 |
| acaggcgttg tagtttgtac tggtgacgaa actcagtgtt acggtacatg ggttcctatt | 180 |
| gggcttgcta tccctgaaaa tgagggtggt ggctctgagg gtggcggttc tgagggtggc | 240 |
| ggttctgagg gtggcggtac taaacctcct gagtacggtg atacacctat tccgggctat | 300 |
| acttatatca accctctcga cggcacttat ccgcctggta ctgagcaaaa ccccgctaat | 360 |
| cctaatcctt ctcttgagga gtctcagcct cttaatactt tcatgtttca gaataatagg | 420 |
| ttccgaaata ggcagggggc attaactgtt tatacgggca ctgttactca aggcactgac | 480 |
| cccgttaaaa cttattacca gtacactcct gtatcatcaa aagccatgta tgacgcttac | 540 |
| tggaacggta aattcagaga ctgcgctttc cattctggct ttaatgagga tttatttgtt | 600 |
| tgtgaatatc aaggccaatc gtctgacctg cctcaacctc ctgtcaatgc tggcggcggc | 660 |
| tctggtggtg gttctggtgg cggctctgag ggtggtggct ctgagggtgg cggttctgag | 720 |
| ggtggcggct ctgagggagg cggttccggt ggtggctctg gttccggtga ttttgattat | 780 |
| gaaaagatgg caaacgctaa taagggggct atgaccgaaa atgccgatga aaacgcgcta | 840 |
| cagtctgacg ctaaaggcaa acttgattct gtcgctactg attacggtgc tgctatcgat | 900 |
| ggtttcattg gtgacgtttc cggccttgct aatggtaatg gtgctactgg tgattttgct | 960 |
| ggctctaatt cccaaatggc tcaagtcggt gacggtgata attcaccttt aatgaataat | 1020 |
| ttccgtcaat atttaccttc cctccctcaa tcggttgaat gtcgcccttt tgtctttggc | 1080 |
| gctggtaaac catatgaatt ttctattgat tgtgacaaaa taaacttatt ccgtggtgtc | 1140 |
| tttgcgtttc ttttatatgt tgccaccttt atgtatgtat tttctacgtt tgctaacata | 1200 |
| ctgcgtaata aggagtct | 1218 |

<210> SEQ ID NO 25
<211> LENGTH: 224
<212> TYPE: PRT
<213> ORGANISM: Artificial sequence
<220> FEATURE:
<223> OTHER INFORMATION: Synthetic Construct

<400> SEQUENCE: 25

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

```
Ala Met His Trp Val Arg Gln Ala Pro Gly Lys Gly Leu Glu Trp Val
             35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

<210> SEQ ID NO 26
<211> LENGTH: 214
<212> TYPE: PRT
<213> ORGANISM: Artificial sequence
<220> FEATURE:
<223> OTHER INFORMATION: Synthetic Construct

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 672
<212> TYPE: DNA
<213> ORGANISM: Artificial sequence
<220> FEATURE:
<223> OTHER INFORMATION: Synthetic Construct

<400> SEQUENCE: 27
gaggtgcagc tggtggagtc tgggggaggc ttggtacagc ctggggaggtc cctgagactc      60 tcctgtgcag cctctggatt cacctttgat gactatgcca tgcactgggt ccgccaggct     120
ccagggaagg gctgagtg gtgtcagct attacttgga atagtggtca catagactac        180
gcagactccg tgagggccg gttcaccatc tccagagaca atgccaagaa ctccctgtat       240
ctgcaaatga acagcctgag agccgaggac acggccgtat attactgtgc gaaagtgagc     300
tacctgagta ctgcctccag cctggactac tggggccaag aaccctggt caccgtctcc      360 tcagcctcca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaagcagag     660
cccaaatctt gc                                                         672

<210> SEQ ID NO 28
<211> LENGTH: 642
<212> TYPE: DNA
<213> ORGANISM: Artificial sequence
<220> FEATURE:
<223> OTHER INFORMATION: Synthetic Construct

<400> SEQUENCE: 28
gacatccaga tgacccagtc tccatcctcc ctgtctgcat ctgtaggaga cagagtcacc      60
atcacttgcc gggcgagtca gggcattcgc aattatttag cctggtatca gcagaaacca    120
gggaaagctc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaacgc tataaccgtg ccccttacac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gc                       642

```
<210> SEQ ID NO 29
<211> LENGTH: 21
<212> TYPE: PRT
<213> ORGANISM: Artificial sequence
<220> FEATURE:
<223> OTHER INFORMATION: Synthetic Construct

<400> SEQUENCE: 29

Val Lys Gln Ser Thr Ile Ala Leu Ala Leu Leu Pro Leu Leu Phe Thr
1               5                   10                  15

Pro Val Ala Lys Ala
            20

<210> SEQ ID NO 30
<211> LENGTH: 63
<212> TYPE: DNA
<213> ORGANISM: Artificial sequence
<220> FEATURE:
<223> OTHER INFORMATION: Synthetic Construct

<400> SEQUENCE: 30
gtgaaacaaa gcactattgc actggcactc ttaccgttac tgtttacccc tgtcgcaaaa      60
gcc                                                                   63

<210> SEQ ID NO 31
<211> LENGTH: 10
<212> TYPE: PRT
<213> ORGANISM: Artificial sequence
<220> FEATURE:
<223> OTHER INFORMATION: Synthetic Construct

<400> SEQUENCE: 31

Tyr Pro Tyr Asp Val Pro Asp Tyr Ala Ser
1               5                   10

<210> SEQ ID NO 32
<211> LENGTH: 30
<212> TYPE: DNA
<213> ORGANISM: Artificial sequence
<220> FEATURE:
<223> OTHER INFORMATION: Synthetic Construct

<400> SEQUENCE: 32
tacccgtacg acgttccgga ttatgccagc                                      30

<210> SEQ ID NO 33
<211> LENGTH: 5
<212> TYPE: PRT
<213> ORGANISM: Artificial sequence
<220> FEATURE:
<223> OTHER INFORMATION: Synthetic Construct

<400> SEQUENCE: 33

Gly Gly Gly Ser Gly
1               5

<210> SEQ ID NO 34
<211> LENGTH: 17
<212> TYPE: PRT
<213> ORGANISM: Artificial sequence
<220> FEATURE:
<223> OTHER INFORMATION: Synthetic Construct
```

```
<400> SEQUENCE: 34

Ala Glu Ala Ala Ala Lys Glu Ala Ala Lys Glu Ala Ala Ala Lys
1               5                   10                  15

Ala

<210> SEQ ID NO 35
<211> LENGTH: 22
<212> TYPE: PRT
<213> ORGANISM: Artificial sequence
<220> FEATURE:
<223> OTHER INFORMATION: Synthetic Construct

<400> SEQUENCE: 35

Ala Glu Ala Ala Ala Lys Glu Ala Ala Lys Glu Ala Ala Ala Lys
1               5                   10                  15

Ala Gly Gly Gly Gly Ser
            20

<210> SEQ ID NO 36
<211> LENGTH: 22
<212> TYPE: PRT
<213> ORGANISM: Artificial sequence
<220> FEATURE:
<223> OTHER INFORMATION: Synthetic Construct

<400> SEQUENCE: 36

Ala Glu Ala Ala Ala Lys Glu Ala Ala Lys Glu Ala Ala Ala Lys
1               5                   10                  15

Ala Gly Pro Pro Gly Pro
            20
```

PHAGE DISPLAY VECTORS AND METHODS OF USE

REFERENCE TO AN ELECTRONIC SEQUENCE LISTING

The contents of the electronic sequence listing (X20314SequenceListing.txt; Size: 56,625 bytes; and Date of Creation: May 15, 2018) is herein incorporated by reference in its entirety.

The present invention is in the field of phage display technologies. More particularly, the present invention relates to vectors suitable for use in displaying fusion proteins comprising the surface protein P.III on the surface of bacteriophage M13 particles, as well as methods of use and compositions comprising the same.

Current phage display techniques allow for the generation and display of heterogenous peptide libraries on the surface of bacteriophage particles. The principle of phage display is based on the presentation of a peptide of interest as part of a fusion protein with a bacteriophage surface coat protein. Briefly, a nucleotide sequence encoding the peptide of interest is cloned in-frame with a gene encoding a phage surface coat protein to generate a fusion product which is expressed or 'displayed' as part of the coat surface upon phage assembly. The expressed peptide library may then be screened against a target or antigen to identify potential peptide ligands for further optimization or affinity maturation.

Bacteriophage M13 is an example of a commonly used phage for expression of heterogenous peptides and antibody fragments via phage display. Filamentous M13 bacteriophage assembly occurs in the bacterial inner membrane. Phage coat proteins are synthesized in the cytoplasm using bacterial protein synthetic machinery and are then directed to the periplasm by different signal peptides. Functional M13 phage particles comprise five types of surface coat proteins termed. P.III, P.VI, P.VII, P.VIII, and P.IX. While all five of these proteins have been used to display exogenous peptides on the surface of M13 particles, the minor coat protein P.III is the most commonly used for anchoring peptides of interest to the phage coat surface, (Methods in Molecular Biology, Vol, 178, *Antibody Phage Display: Methods and Protocols*, edited by O'Brien and Aitken) P.III exists in five copies at the proximal end of the M13 phage and plays important roles in phage infectivity, assembly, and stability. P.III is expressed as a 406 amino acid polypeptide and is comprised of three distinct regions: N1, N2, and C-terminal (CT) domains (Russel et al., *Introduction to Phage Biology and Display*, Phage Display: A Laboratory Manual; Cold Spring Harbor Lab. Press.) The N1 domain participates in translocation of the viral DNA into the bacterial (*E. coli*) host during infection, while the N2 domain imparts host cell recognition by attaching to bacterial F pilus. The CT domain participates in anchoring the P.III protein to the phage coat during assembly. (Omidfar et al, *Advances in Phage Display Technology for Drug Discovery*, Expert Opin. Drug Discov, (2015)).

Phage display systems may be classified according to the type of vector used for bacterial host cell infection. For display of P.III fusion products, type 3 and type 33 vectors are commonly used.(Omidfar et at (2015)). The type 3 vector comprises one copy of the gene encoding the P.III protein (the g.III gene), to which a gene encoding an exogeonous peptide of interest may cloned in-frame. As a result, each peptide is displayed on the phage in five copies, each in fusion with an expressed P.III protein. While use of type 3 vectors are an efficient way to display short peptides, for example 12 amino acids or less, display of longer peptides substantially reduces phage infectivity and therefore its amplification (titer), thus preventing construction of highly diverse peptide libraries. The type 33 vector comprises two copies of the g.III gene—the wild type copy and a recombinant copy. The wild-type and recombinant g.III genes encode P.III proteins having the same amino acid sequence, however they differ in nucleotide sequence and are expressed using different signal peptide sequences. For example, P.III protein encoded by the wild-type g.III may be expressed with the endogenous 18-amino acid signal sequence, whereas P.III encoded by the recombinant g.III may be expressed with a periplasmic signal sequence.

Using the type-33 system, the gene encoding the exogenous protein or peptide can be cloned in-frame with one copy of the g.III gene (i.e., the wild-type or recombinant gene), allowing for display of the peptide of interest with reduced steric hindrance on the phage coat surface. Thus, the type-33 vector is tolerant of displaying larger exogenous peptides, albeit at a lower copy number. The lower copy number, however, creates a limitation for successful isolation of target-specific peptides because peptides, prior to affinity maturation, suffer from lower affinity to their targets. Lower affinity, combined with lower display levels, hampers the detection of target-specific peptides from a large pool of peptide variants.

In accordance with the present invention, an improved system of type-33 phage vectors and methods of use have been identified such that peptides, for example peptides up to 35 amino acids in length, can be successfully displayed on the M13 phage surface in multiple copies. In this system, improved display of the peptide of interest is achieved by introducing defined mutations in the wild type g.III gene. These mutations reduce the incorporation of the polypeptide encoded by the mutated wild type g.III gene on the phage surface. As a consequence, higher copies of P.III protein encoded by the recombinant g.III gene are displayed on the phage. This results in a higher display level of an exogenous peptide of interest when fused or cloned in-frame to the recombinant g.III gene product. Furthermore, the vectors and methods of the present invention allow for the generation of bacteriophage M13 particles which maintain phage infectivity at levels comparable to wild-type bacteriophage M13 when peptides of up to 35 amino acids in length are displayed on phage coat surface.

Thus, the present invention provides a type 33 bacteriophage M13 vector comprising a first polynucleotide sequence encoding a polypeptide sequence as given by SEQ ID NO:1 and a second polynucleotide sequence encoding a polypeptide sequence as given by SEQ NO:2. As a particular embodiment to the afore-mentioned bacteriophage M13 vector, said first polynucleotide sequence is given by SEQ ID NO:3 and said second polynucleotide sequence is given by SEQ NO:4. As another particular embodiment to the afore-mentioned vectors, said vector further comprises a polynucleotide sequence encoding a suitable detection tag sequence cloned in-frame with and upstream of the polynucleotide sequence encoding the polypeptide sequence as given by SEQ ID NO:1. As a further particular embodiment to the afore-mentioned vector, said vector comprises the polynucleotide sequence as given by SEQ ID NO:15. As an even further particular embodiment to any of the afore-mentioned vectors, said vector is a double stranded polynucleotide molecule.

As another embodiment, the present invention provides any of the type 33 bacteriophage M13 vectors as described above, further comprising a polynucleotide sequence encoding an exogenous polypeptide, and particularly an exogenous polypeptide of up to 35 amino acids in length, cloned in-frame with and upstream of the polynucleotide sequence encoding the polypeptide sequence as given by SEQ ID NO:1, or upstream of the polynucleotide sequence encoding the suitable detection tag sequence. More particularly, the polynucleotide sequence encoding the exogenous peptide is cloned in-frame with the polynucleotide sequence encoding the polypeptide sequence as given by SEQ ID NO:1, or with the polynucleotide sequence encoding the suitable detection tag sequence, via a polynucleotide sequence encoding a peptide linker upstream of the polynucleotide sequence encoding the polypeptide sequence as given by SEQ ID NO:1 or the polynucleotide sequence encoding the suitable detection tag sequence. More particularly, the exogenous polypeptide is between 7 and 35 amino acids in length.

In yet another embodiment, the present invention provides a method for producing a bacteriophage M13 particle comprising: (a) transfecting a bacterial host cell with a double stranded type 33 bacteriophage M13 vector comprising a first polynucleotide sequence encoding a polypeptide sequence as given by SEQ ID NO:1 and a second polynucleotide sequence encoding a polypeptide sequence as given by SEQ ID NO:2, (b) incubating said bacterial host cell under conditions suitable for expression of said first and second polynucleotide sequences and assembly of bacteriophage M13 particles in said bacterial host cell, and (c) recovering from said bacterial host cell a bacteriophage M13 particle comprising polypeptide sequences given by the amino acid sequences of SEQ ID NO:1 and SEQ ID NO:2 independently displayed on the bacteriophage M13 coat surface. More particular to this embodiment, said first polynucleotide sequence is given by SEQ ID NO:3 and said second polynucleotide sequence is given by SEQ ID NO:4. As another particular embodiment, the present invention provides any of the afore-mentioned methods wherein the double stranded bacteriophage M13 vector further comprises a polynucleotide sequence encoding a suitable detection tag sequence cloned in-frame with and upstream of the polynucleotide sequence encoding the polypeptide sequence as given by SEQ ID NO:1. As yet another particular embodiment, the double stranded bacteriophage M13 vector comprises the polynucleotide sequence as given by SEQ ID NO:15. Even more particular, the present invention provides any of the afore-mentioned methods wherein the double stranded M13 vector further comprises a polynucleotide sequence encoding an exogenous polypeptide, and particularly an exogenous polypeptide of up to 35 amino acids in length, cloned in-frame with and upstream of the polynucleotide sequence encoding the polypeptide sequence as given by SEQ ID NO:1, or upstream of the polynucleotide sequence encoding the suitable detection tag sequence. As another particular embodiment, the polynucleotide encoding the exogenous polypeptide is cloned in-frame with the polynucleotide sequence encoding the polypeptide sequence as given by SEQ ID NO:1, or with the polynucleotide sequence encoding the suitable detection tag sequence, via a polynucleotide sequence encoding a peptide linker upstream of the polynucleotide sequence encoding the polypeptide sequence as given by SEQ ID NO:1, or the polynucleotide sequence encoding the suitable detection tag sequence. More particularly, the exogenous polypeptide is between 7 and 35 amino acids in length. As another particular embodiment to afore-mentioned methods, the bacterial host cell is an F+ bacterial strain such as an XL-1 Blue E.coli cell or XLO E.coli cell.

In yet another embodiment, the present invention provides a bacteriophage M13 particle wherein said particle comprises the polypeptide sequences given by the amino acid sequences of SEQ ID NO:1 and SEQ ID NO:2, displayed independently on the phage particle coat surface. More particular, the present invention provides the afore-mentioned bacteriophage M13 particle wherein said particle further comprises a suitable detection tag sequence fused to the N-terminus of the polypeptide sequence given by the amino acid sequence of SEQ ID NO:1. More particular still, the present invention provides any of the afore-mentioned bacteriophage M13 particles wherein said particle further comprises an exogenous polypeptide, and particularly an exogenous polypeptide of up to 35 amino acids in length, fused to the N-terminus of the polypeptide sequence given by the amino acid sequence of SEQ ID NO:1, or to the N-terminus of the suitable detection tag sequence. In another particular embodiment, the exogenous polypeptide is fused to the polypeptide sequence given by the amino acid sequence of SEQ ID NO:1, or to the suitable detection tag sequence, via a peptide linker fused to the N-terminus of the polypeptide sequence given by SEQ ID NO:1, or to the N-terminus of the suitable detection tag sequence, and the C-terminus of the exogenous polypeptide. More particularly, the exogenous polypeptide fused to the polypeptide sequence given by SEQ ID NO:1, or to the detection tag sequence, is between 7 and 35 amino acids in length.

In yet another embodiment, the present invention provides a method for infecting a bacterial host cell comprising contacting said bacterial host cell with a bacteriophage M13 particle comprising the polypeptide sequences given by the amino acid sequences of SEQ ID NO:1 and SEQ ID NO:2 independently displayed on the bacteriophage M13 particle coat surface. More particular, the present invention provides the afore-mentioned method wherein said bacteriophage M13 particle further comprises a suitable detection tag sequence fused to the N-terminus of the polypeptide sequence given by SEQ ID NO:1. More particular still, the present invention provides any of the afore-mentioned methods wherein said bacteriophage M13 particle further comprises an exogenous polypeptide, and particularly an exogenous polypeptide of up to 35 amino acids in length, fused to the N-terminus of the polypeptide sequence given by SEQ ID NO:1, or to the N-terminus of the suitable detection tag sequence. More particular, the exogenous polypeptide is fused to the polypeptide sequence given by SEQ ID NO:1, or to the suitable detection tag sequence, via a peptide linker fused to the N-terminus of the polypeptide sequence given by SEQ ID NO:1, or to the N-terminus of the suitable detection tag sequence, and the C-terminus of the exogenous polypeptide. More particularly, the exogenous polypeptide fused to the polypeptide sequence given by SEQ ID NO:1, or to the detection tag sequence, is between 7 and 35 amino acids in length. As another particular embodiment to afore-mentioned methods, the bacterial host cell is an F+ bacterial strain such as XL-1 Blue E.coli cell or XLO E.coli cell.

When using a type-33 bacteriophage M13 vector for expression and display of P.III protein fusion products, the P.III proteins encoded by the wild-type and recombinant g.III genes compete for assembly into the phage particles. Previous work in the field demonstrated that modification of the cleavage site in the c-region and some residues in the h-region of Sec signal sequences could result in enhanced expression of antibody fragments displayed on phage particles using a 3+3 vector system. (Lee et al., Biochemical and Biophysical Research Communications, 411 (2011); 348-353) In contrast to the prior art, the objective of the present invention is to influence the ratio of the gene products encoded by the wild-type and recombinant g.III genes expressed in the periplasm in favor of the P.III protein encoded by the recombinant g.III gene. As a consequence of the present invention, an increase in the relative expression and display of P.III protein encoded by the recombinant gene is achieved which, in turn, results in an increased display of exongenous peptides when nucleotide sequences encoding such exogenous peptides are cloned in-frame with the recombinant g.III gene.

Definitions

"Vector", as used herein, refers to a nucleic acid molecule capable of transporting another nucleic acid sequence (or multiple nucleic acid sequences) to which it has been ligated into a host cell or genome. One type of vector is a "plasmid", which refers to a circular DNA loop, typically double stranded, into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication.) Moreover, certain vectors are capable of directing the expression of genes (for example genes encoding an exogenous peptide or protein of interest) to which they are operatively linked when combined with appropriate control sequences such as promoter and operator sequences and replication initiation sites. Such vectors are commonly referred to as "expression vectors" and may also include a multiple cloning site for insertion of the gene encoding the protein of interest. Alternatively, the gene encoding the peptide or protein of interest may be introduced by site-directed mutagenesis techniques such as Kunkel mutagenesis. (Handa et al., *Rapid and Reliable Site-Directed Mutagenesis Using Kunkel's Approach*, Methods in Molecular Biology, vol 182: In Vitro Mutagenesis Protocols, $2^{nd}$ Ed.).

"Type 33 bacteriophage M13 vector", as used herein, refers to a "Vector" capable of transporting nucleic acid sequences of the bacteriophage M13 genome into host cells or genomes and comprises coding regions for two copies of the P.III surface protein (i.e., a wild-type and recombinant g.III gene) in addition to coding regions for each of the remaining proteins (P.I, P.II, P.IV-P.XI) encoded by the bacteriophage M13 genome. The Type 33 bacteriophage M13 vectors of the present invention contain mutations in the wild-type copy of the g.III gene which encode a polypeptide having a different amino acid sequence from the P.III surface protein encoded by the (unmutated) wild-type g.III and recombinant g.III genes An "Exogenous" or "foreign" peptide, polypeptide or protein refers to a peptide, polypeptide or protein encoded by a nucleic acid sequence not normally present in the host cell or genome from which the nucleic acid is to be expressed.

"Suitable detection tag" or "suitable detection tag sequence", as used herein, refers to a peptide sequence which may be grafted or fused to another protein or peptide of interest through recombinant techniques. Grafting of the tag sequence to the protein of interest allows detection of the protein, for example, by use of antibodies directed to the tag peptide sequence. Determination of suitable detection tag sequences is well within the knowledge of those skilled in the art. Typical detection tag sequences suitable for use in the present invention include c-myc tag, HA-tag, His-tag, Flag-tag and S-tag.

"Cloned in-frame", as used herein, refers to the insertion of a nucleic acid sequence (for example a nucleic acid sequence encoding a particular polypeptide of interest) into the same open reading frame of a reference nucleic acid or gene (for example, a gene encoding a separate protein to which the polypeptide of interest is to be fused.) As one of skill in the art will appreciate, the insertion nucleic acid may be inserted contiguous with the reference gene or it may be inserted at a spatially separated site through use of a linker encoding sequence also cloned in-frame. Further, the insertion nucleic acid may be inserted either upstream or downstream of the reference nucleic acid sequence. As used herein, "upstream" refers to the placement or location of a nucleic acid sequence of interest relative to a reference nucleic acid or gene such that the sequence of interest is translated prior to the reference nucleic acid or gene during translation. Likewise, "downstream" as used herein, refers to the placement or location of a nucleic acid sequence of interest relative to a reference nucleic acid or gene such that the sequence of interest is translated after the reference nucleic acid or gene during translation.

"Peptide linker" as used herein refers to a polypeptide sequence that fuses or links a first peptide or protein to a second peptide or protein. The N-terminus of the linker polypeptide sequence is covalently attached to the C-terminus of the first peptide or protein through an amide bond while the C-terminus of the linker polypeptide sequence is covalently attached to the N-terminus of the second peptide or protein, also through an amide bond. Typical peptide linkers suitable for use in the present invention include serine containing peptides such as -$(G_3SG)_n$- and -$(G_4S)_n$-peptide sequences, and α-helix linkers such as -AEAAAKEAAAKEAAAKA- (SEQ NO:34), -AEAAAKEAAAKEAAAKAGGGGS- (SEQ. ID NO:35), and -AEAAAKEAAAKEAAAKAGPPGP- (SEQ NO:36).

The polypeptide chains as disclosed herein are depicted by their sequence of amino acids from N-terminus to C-terminus, when read from left to right, with each amino acid represented by either their single letter or three-letter amino acid abbreviation. The "N-terminus" (or amino terminus) of an amino acid, or a polypeptide chain, refers to the free amine group on the amino acid, or the free amine group on the first amino acid residue of the polypeptide chain. Likewise, the "C-terminus" (or carboxy terminus) of an amino acid, or a polypeptide chain, refers to the free carboxy group on the amino acid, or the free carboxy group on the final amino acid residue of the polypeptide chain.

Vector Engineering

Using Kunkel mutagenesis (Handa et al., *Rapid and Reliable Site-Directed Mutagenesis Using Kunkel's Approach*, Methods in Molecular Biology, vol 182.: In Vitro Mutagenesis Protocols, $2^{nd}$ Ed,), the first sixty seven amino acids of the N1 region of the P.III protein encoded by the wild type g.III gene are randomized to different amino acids while monitoring display level of a detection tag sequence, for example c-myc protein (EQKLISEEKL: SEQ ID NO:7), fused to the P.III protein encoded by the recombinant g.III gene. The nucleotide sequence encoding the detection tag sequence, for example the c-myc encoding sequence (gagcaaaagctcattagtgaagaggatctt: SEQ ID NO:8), is cloned in-frame with the recombinant g.III gene. *Escherichia coil* strain RZ1032, (ATCC 39737) which lacks functional dUTPase and uracil glycosylase, is used to prepare uracil containing single-stranded DNA of the parent type 33 bacteriophage M13 vector (SEQ ID NO:6). The sixty seven mutagenic primers are divided into four different Kunkel reactions, with three reactions covering seventeen mutations and one reaction covering sixteen mutations. Each primer in a reaction group contains an NNK codon corresponding to the amino acid to be fully randomized and are designed to share the same flanking sequence to the parent vector to ensure that all primers will anneal to the template with comparable efficiency.

Following mutation of the parent vector, the modified vectors are used as templates to prepare a double stranded DNA which is then transfected into bacterial host cells (for example, E.Coli XL1-Blue cells) by electroporation for expression of bacteriophage M13 particles. Prior to screening the M13 phage libraries, random phage from each library are sequenced to ensure that each position is fully randomized to all 20 amino acids without any bias for a particular amino acid.

Phage Harvest and Titer Determination

After an overnight amplification, phage may be harvested as follows: Infected bacterial host cells (for example, XL-1 Blue cells) are centrifuged at 3,000 rpm for about 20 minutes. 40 ml of supernatant is then transferred to a fresh flask and the phage are precipitated by addition of 10 mL of a PEG Solution (20% PEG including 3.5 M NH4OAc) and incubation at 4° C. for about 90 minutes. The mixture is then centrifuged at 13,000 rpm for about 45 min. The pellet is then resuspended in 1 ml of PBS (phosphate buffer saline, pH 7.4) and centrifuged for 5 minutes at 13,000 rpm to remove residual cell debris. The supernatant is then transferred to a fresh tube, 200 µl of the PEG solution is added, and the mixture is incubated on ice for about 30 min. The mixture is then spun down at 13,000 rpm for about 45 min at 4° C. The resulting pellet is resuspended in 200-500 µl of PBS and centrifuged at 13,000 rpm for about 5 min. to remove residual cell debris. The supernatant is then transferred to a fresh tube and centrifugation process is repeated until no bacterial cell residue is present.

The supernatant may then be transferred to a fresh tube for titer determination as follows: Serial dilutions of the phage-containing supernatant are prepared and 100 µl of each dilution is then added to a new tube followed by addition of 300 µl of bacterial cells (for example, XL1-Blue cells) that have been allowed to grow overnight. The mixture is incubated at room temperature for about 15 minutes then 3 ml of soft agar is added to each tube. (Soft agar may be prepared as follows: Fill a 250 ml bottle with 50 ml of lysogeny broth (LB), add 2.08 Bacto Agar powder (Fisher DF0140-01-1) then swirl to mix. Q.S. mixture to 250 ml with additional LB, autoclave for 45 min. and store at 55° C.) The mixture is vortexed briefly then added to LB plates and incubated overnight at 37° C. The resulting plaques are then counted and titer determined as plaque-forming units (pfu).

Phage Infection and Amplification

For amplification of particular phage clones, the following procedures may be employed: A single colony of bacterial host cells (for example, XL1-Blue cells (Stratagene)) is grown in 50 ml of 2YT media supplemented with tetracycline at 37° C. while shaking to a density of 0.4-0.6 $OD_{600}$. Approximately $10^8$ pfu (plaque forming units) of phage are added to the bacterial culture and the mixture is then incubated at 37° C. for about 30 minutes while standing to allow for phage infection. The infected cell culture is then incubated at 37° C. for 12-15 hours while shaking to allow phage amplification.

Bacteriophage M13 Screening

Capture Filter Lift Assay:

To identify mutations that result in higher display of c-myc fused to P.III protein encoded by the recombinant g.III gene, a capture filter-lift assay may be used (Wu, *Simultaneous Humanization and Affinity Optimization of Monoclonal Antibodies*, Methods in Molecular biology, Vol, 2017. Recombinant Antibodies for Cancer Therapy: Methods and Protocols, edited by Weischof and Krauss). Briefly, nitrocellulose filters are coated with 2 µg/ml of an anti-bacteriophage M13 antibody (GE Biosciences 27-9420-01) and then blocked with casein prior to the plaque lift. The c-myc display level is detected by an anti c-myc antibody-alkaline phosphatase conjugate (SIGMA A5963) with plaques displaying a higher display level of c-myc protein appearing with darker color. Plaques with higher display levels of the c-myc tag are then isolated for sequencing. Sequenced M13 phage bearing mutations that resulted in stronger c-myc signal may be amplified for further screening, including single-point and phage titer-dependent ELSIAs, as further described below Single-Point and Phage Titer-Dependent ELISA:

For single point ELISA, individual bacteriophage M13 phage with enhanced c-myc display level (identified, for example by filter lift assay) are amplified overnight using 2-ml XL1-blue bacterial culture. Following amplification, the culture is spun down and the supernatant (containing the phage) is used in the assay. Briefly, ELISA plates are coated overnight with an anti-bacteriophage M13 antibody (GE Biosciences 27-9420-01) and blocked with casein. M13 phage-containing supernatant is added and c-myc display is detected by an anti c-myc antibody conjugated to alkaline phosphatase (SIGMA A5963). C-myc display levels are determined by spectrophotometry by measuring OD at the appropriate wavelength, using an appropriate substrate. Phage demonstrating higher c-myc peptide display levels may be further confirmed in a titer-dependent phage ELISA where the c-myc display level for individual clones is determined over a range of titers and compared with the c-myc display level for clones obtained by transfection with parental vector (i.e., vector containing the wild type g.III gene (without mutations), and c-myc protein cloned in frame with the recombinant g.III gene)

EXAMPLE 1

Display of c-myc tag-P.III Fusion on Bacteriophage M13 Surface

Using a type-33 bacteriophage M13 parent vector comprising both a wild-type g.III gene (SEQ ID NO:5) and a recombinant g.III gene (SEQ ID NO:3) under control of a lacZ promoter, each gene encoding a copy of the P.III surface protein and using nucleotide sequences encoding the endogenous P.III and pelB signal peptides, respectively (SEQ ID NOs:17 and 19), single amino acids in the N1 region of the wild-type g.III are randomized essentially as described above. Modified vectors comprising mutations which encode L8P or S11P substitutions in the mature wild-type g.III gene product are constructed and transfected into *E.Coli l XL*1-Blue cells to express a c-myc tag-encoding sequence (SEQ ID NO:8) cloned in-frame with and upstream of the recombinant g.III gene. The resulting P.III-c-myc fusion protein is displayed on the surface of harvested M13 particles and c-myc display levels are detected by a phage-titer dependent ELISA essentially as described above.

Table 1, below, provides the nucleic acid sequences of the parental and mutated wild-type g.III genes, the recombinant g.III gene, the c-myc tag-encoding sequence, the signal peptide-encoding sequences and the resulting amino acid sequences encoded thereby. Table 2 provides the results of the phage-titer dependent ELISA.

TABLE 1

Nucleic acid sequences

| Vector component | Parental vector, (wild type g.III gene) | Mutated vector (wild-type g.III gene encoding L8P substitution) | Mutated vector (wild-type g.III gene encoding S11P substitution) |
|---|---|---|---|
| WT g.III gene | SEQ ID NO: 5 | SEQ ID NO: 23 | SEQ ID NO: 24 |
| Recombinant g.III gene | SEQ ID NO: 3 | SEQ ID NO: 3 | SEQ ID NO: 3 |
| c-myc tag gene | SEQ ID NO: 8 | SEQ ID NO: 8 | SEQ ID NO: 8 |
| WT g.III signal sequence | SEQ ID NO: 17 | SEQ ID NO: 17 | SEQ ID NO: 17 |
| Recombinant g.III signal sequence | SEQ ID NO: 19 | SEQ ID NO: 19 | SEQ ID NO: 19 |

Encoded amino acid sequences

| Encoded product | Parental vector, (wild type g.III gene) | Mutated vector (wild-type g.III gene encoding L8P substitution) | Mutated vector (wild-type g.III gene encoding S11P substitution) |
|---|---|---|---|
| WT g.III gene product | SEQ ID NO: 1 | SEQ ID NO: 21 | SEQ ID NO: 22 |
| Recombinant g.III gene product | SEQ ID NO: 1 | SEQ ID NO: 1 | SEQ ID NO: 1 |
| c-myc tag | SEQ ID NO: 7 | SEQ ID NO: 7 | SEQ ID NO: 7 |
| WT g.III signal peptide | SEQ ID NO: 18 | SEQ ID NO: 18 | SEQ ID NO: 18 |
| Recombinant g.III signal peptide | SEQ ID NO: 20 | SEQ ID NO: 20 | SEQ ID NO: 20 |

TABLE 2

| Phage titer (pfu/well) | Parental, wild type g.III gene ($OD_{560}$) | Mutated, wild-type g.III gene encoding L8P substitution ($OD_{560}$) | Mutated, wild-type g.III gene encoding S11P substitution ($OD_{560}$) |
|---|---|---|---|
| 0 | 0.1364 | 0.1057 | 0.137 |
| 7.80E+06 | 0.1473 | 0.126 | 0.1434 |
| 1.60E+07 | 0.1449 | 0.1356 | 0.1357 |
| 3.10E+07 | 0.1451 | 0.1381 | 0.1423 |
| 6.30E+07 | 0.1663 | 0.1422 | 0.159 |
| 1.30E+08 | 0.1505 | 0.1488 | 0.1711 |
| 2.50E+08 | 0.142 | 0.1629 | 0.1887 |
| 5.00E+08 | 0.1777 | 0.1949 | 0.2283 |
| 1.00E+09 | 0.1753 | 0.2347 | 0.2805 |
| 2.00E+09 | 0.2047 | 0.4117 | 0.4519 |
| 4.00E+09 | 0.3157 | 0.8489 | 0.9137 |

Table 2 provides $OD_{560}$ values from a titer-dependent ELISA as generally described above using a PMP/AMP substrate and demonstrates that when using a type 33 M13 phage vector containing mutations that encode L8P or S11P substitutions in the mature, wild type g.III gene product, increased expression of a c-myc protein fused to the P.III surface protein encoded by the recombinant g.III gene is obtained.

EXAMPLE 2

Display of Test Peptide-P.III Fusions on Phage M13 Surface (with Combined 8P+11P Mutations in WT g.III Gene)

Further modified type-33 bacteriophage M13 vectors comprising mutations which encode both the L8P and S11P substitutions in the mature wild-type g.III gene product (SEQ ID NO:2) are constructed. An exemplary nucleic acid sequence encoding said gene product is given by SEQ ID NO:4. In the same vectors, test peptide-encoding nucleic acid sequences (as given by SEQ ID NOs: 10, 12 and 14, below) are separately cloned in-frame, via linker peptide-encoding sequences, to a c-myc tag-encoding sequence (SEQ ID NO:8) which, in turn, is cloned in frame with and upstream of the recombinant g.III gene sequence (SEQ ID NO:3) in the vector. The same test peptide-encoding nucleic acid sequences are also each separately cloned (in the same manner and format as described above) into the parental type-33 bacteriophage M13 vector which does not comprise either the L8P- or S11P-encoding nucleic acid mutations in the wild type g.III gene (SEQ ID NO:5 provides the nucleic acid sequence of the parental wild type g.III gene without the the L8P- or S11P-encoding mutations).

Table 3 provides the nucleic acid sequences of the mutated and parental wild-type g.III gene, the recombinant g.III gene, the c-myc tag encoding sequence, the linker peptide encoding sequences and the test peptide-encoding sequences of exemplary vector clones prepared.

The resulting vectors were used to display the test peptide—P.III fusion proteins on the surface of M13 bacteriophage particles harvested from XL-1 blue bacterial cells. The test peptides employed bind with a human IL-6 target protein as further described below. Table 4 provides the corresponding amino acid sequences of the components of the fusion protein products displayed on the harvested M13 phage particles.

TABLE 3

Vector Clone

| Nucleic Acid Component | 18-24[a] | 18-22[a] | 18-4[a] |
|---|---|---|---|
| Mutated wild type g.III gene | (SEQ ID NO: 4) | (SEQ ID NO: 4') | (SEQ ID NO: 4) |
| Parental wild type g. III gene | (SEQ ID NO: 5) | (SEQ ID NO: 5) | (SEQ ID NO: 5) |
| Recombinant g.III gene | (SEQ ID NO: 3) | (SEQ ID NO: 3) | (SEQ ID NO: 3) |

TABLE 3-continued

Vector Clone

| Nucleic Acid Component | 18-24[a] | 18-22[a] | 18-4[a] |
|---|---|---|---|
| c-myc encoding sequence | (SEQ ID NO: 8) | (SEQ ID NO: 8) | (SEQ ID NO: 8) |
| Peptide linker encoding sequence | (SEQ ID NO: 16) | (SEQ ID NO: 16) | (SEQ ID NO: 16) |
| Test peptide-encoding sequence | cgcacctatscaaagaatttg gccgctatgtggcggatgaa acctattgcgeggcgctg (SEQ ID NO: 10) | attagcctgtgcgatcagccg tatgtgaaaagcctgaacctg ccgctgtgcccgctggcg (SEQ ID NO: 12) | ccgccgctgtgcagctggcc ggcgtatcagaaatttggcgg cccgctgtgcaccetgggc (SEQ ID NO: 14) |

[a]Vector clones are prepared with either the mutated, wild type g.III gene containing mutations encoding the L8P and S11P substitutions (i.e. SEQ ID NO: 4), or the parental wild type g.III gene (i.e., SEQ ID NO: 5).

TABLE 4

Displayed Fusion Protein

| Amino Acid Component | 18-24[a] | 18-22[a] | 18-4[a] |
|---|---|---|---|
| Mature, mutated wild type g.III gene product | (SEQ ID NO: 2) | (SEQ ID NO: 2) | (SEQ ID NO: 2) |
| Mature, parental wild type g.III gene product | (SEQ ID NO: 1) | (SEQ ID NO: 1) | (SEQ ID NO: 1) |
| Mature, recombinant g.III gene product | (SEQ ID NO: 1) | (SEQ ID NO: 1) | (SEQ ID NO: 1) |
| c-myc detection tag protein | (SEQ ID NO: 7) | (SEQ ID NO: 7) | (SEQ ID NO: 7) |
| Peptide linker sequence | (SEQ ID NO: 33) | (SEQ ID NO: 33) | (SEQ ID NO: 33) |
| Test peptide sequence | RTFCKEFGRYVAD ETYCAAL (SEQ ID NO: 9) | ISLCDQPYVKSLNL PLCPLA (SEQ ID NO:11) | PPLCSWPAYQKFG GPLCTLG (SEQ ID NO: 13) |

[a]Displayed fusion proteins contain either the mutated wild type g.III gene product containing the L8P and S11P substitutions (i.e., SEQ ID NO: 2), or the parental wild type g.III gene product.

Harvested phage displaying the test peptide—P.III fusion proteins are amplified and titer determination performed as generally described above. Test peptide display levels are then determined by a phage-titer dependent ELISA essentially as described below:

ELISA plates (Greiner-bio-one, Cat. number: 650061) are coated with 50 µl/well of NeutrAvidin (Thermo Scientific, Cat. number: 31050) at 2 µg/ml in PBS and allowed to stand overnight at 4° C. Excess sites are blocked by adding 100 µl/well of Casein (Thermo Scientific, Cat number: 37528) for one hour at room temperature. 50 µl/well of biotinylated human IL6 (R&D Systems, Cat. number 206-IL-010/CF) in PBS is then added to each well and the plates are incubated at room temperature for 30 minutes while rocking. 50 µl/well of phage at different titers are then added and the phage diluted in a final concentration of 1% BSA in PBS. Plates are then incubated for 60 minutes at room temperature while rocking. 50 µl/well of anti-M13-HRP (G.E., Cat number: 27-9421-01), diluted 1:5,000 in 0.1% tween in PBS is then added followed by incubation of the plates for 60 minutes at room temperature. 50 of Ultra tetramethylbenzidine substrate (Ultra TMB substrate, Thermo Scientific, Cat number: 34029) is then added and the OD at 650 nm is determined.

Table 5 below provides $OD_{650}$ values obtained over a range of phage titers for phage clones 18-24, 18-22 and 18-4, each prepared separately with the type-33 bacteriophage M13 vector encoding the L8P- and S11P-encoding mutations in the wild type g.III gene and the parental type-33 bacteriophage M13 vector (without the L8P- and S11P-encoding mutations in the wild type g.III gene.)

TABLE 5

| Phage titer (pfu/well) | Phage Clone 18-24 | | Phage Clone 18-22 | | Phage Clone 18-4 | |
|---|---|---|---|---|---|---|
| | Parental[a] ($OD_{650}$) | Mutated[b] ($OD_{650}$) | Parental[a] ($OD_{650}$) | Mutated[b] ($OD_{650}$) | Parental[a] ($OD_{650}$) | Mutated[b] ($OD_{650}$) |
| 2.3E+08 | 0.0735 | 0.3414 | 0.0536 | 0.3284 | 0.0879 | 0.4286 |
| 6.9E+08 | 0.0426 | 0.8103 | 0.0416 | 0.7749 | 0.1359 | 0.988 |
| 2.1E+09 | 0.049 | 1.4618 | 0.0535 | 1.4022 | 0.3378 | 1.5715 |
| 6.2E+09 | 0.0521 | 1.9132 | 0.0605 | 1.8236 | 0.8358 | 1.918 |
| 1.9E+10 | 0.0675 | 2.0298 | 0.1132 | 1.967 | 1.4314 | 2.0064 |
| 5.6E+10 | 0.1189 | 2.0099 | 0.3253 | 1.9578 | 1.756 | 1.8853 |
| 1.7E+11 | 0.2946 | 1.7346 | 0.7754 | 1.7187 | 1.8199 | 1.5817 |
| 5.0E+11 | 0.6837 | 1.5017 | 1.4298 | 1.4979 | 1.6572 | 1.2222 |

[a]Phage clones prepared with type 33 bacteriophage M13 vector containing wild type g.III gene (does not encode L8P and S11P substitutions).
[b]Phage clones prepared with type 33 bacteriophage M13 vector containing mutated, wild type g.III gene encoding L8P and S11P substitutions.

The $OD_{650}$ values in Table 5 demonstrate that when using a type 33 bacteriophage M13 vector containing mutations that encode L8P and S11P substitutions in the mature, wild type g.III gene product, increased expression of each test peptide fused (via a peptide linker) to the P.III surface protein encoded by the recombinant g.III gene is obtained.

EXAMPLE 3

Display of Fab-P.III Fusions on Phage M13 Surface

Nucleic acid sequences encoding Fab heavy chain (HC) and light chain (LC) sequences as given by SEQ ID NO:25 and SEQ ID NO:26, respectively, are cloned into a type-33 bacteriophage M13 vector comprising mutations encoding the L8P and S11P substitutions in the mature wild type g.III gene product. The Fab HC-encoding nucleic acid sequence (SEQ 1D NO:27), using a PhoA1 signal peptide-encoding sequence (SEQ ID NO:30), is cloned in-frame and upstream, via a spacer-encoding sequence, to an HA-tag encoding sequence (SEQ ID NO:32) and a c-myc tag encoding sequence (SEQ ID NO:8) which, in turn, are cloned in frame and upstream of the recombinant g.III gene sequence (SEQ ID NO:3) in the vector. The Fab LC-encoding nucleic acid sequence (SEQ ID NO:28) is separately cloned into the vector using a pelB signal peptide encoding sequence (SEQ ID NO:19). Transcription of both the HC and LC Fab-encoding components is under control of a lacZ promoter.

Double stranded vectors comprising the Fab HC and LC sequences as described above are prepared and used to transfect E.Coli XL1-Blue cells essentially as described previously. The LC sequence (SEQ ID NO:26) is secreted into the bacterial periplasmic space where it forms the Fab dimer with the HC sequence (SEQ ID NO:25) fused via the HA-tag (SEQ ID NO:31) and c-myc tag (SEQ ID NO:7) to the recombinant P.III protein.

Harvested phage displaying the Fab—P.III fusion proteins are amplified and titer determination performed as generally described above. Fab display levels are then determined by a phage-titer dependent ELISA using biotinylated TNFα as the target ligand as generally described in Nakayama et al., *Improving the Copy Number of Antibody Fragment Expressed on the Major Coat Protein of Bacteriophage M13*, Immunotechnology, Vol. 12 (1996): 197-207.

Table 6, below, provides $OD_{650}$ values obtained over a range of phage titers for the phage clone displaying the Fab constructs, prepared separately with the type-33 bacteriophage M13 vector encoding the L8P- and S11P-encoding mutations in the wild type g.III gene and the parental type-33 bacteriophage M13 vector (without the L8P- and S11P-encoding mutations in the wild type g.III gene.)

TABLE 6

| Phage Titer (pfu/well) | Parental[a] ($OD_{650}$) | Phage Titer (pfu/well) | Mutated[b] ($OD_{650}$) |
|---|---|---|---|
| 0 | 0.0699 | 0 | 0.0548 |
| 1.69E+06 | 0.0791 | 1.69E+05 | 0.0846 |
| 5.08E+06 | 0.0857 | 5.08E+05 | 0.1067 |
| 1.52E+07 | 0.0913 | 1.52E+06 | 0.1791 |
| 4.57E+07 | 0.1092 | 4.57E+06 | 0.3578 |
| 1.37E+08 | 0.1712 | 1.37E+07 | 0.7649 |
| 4.12E+08 | 0.3803 | 4.12E+07 | 1.4751 |
| 1.23E+09 | 0.8396 | 1.23E+08 | 1.9562 |
| 3.70E+09 | 1.6574 | 3.70E+08 | 7.2079 |
| 1.11E+10 | 2.2358 | 1.11E+09 | 7.207 |
| 3.33E+10 | 2.4446 | 3.33E+09 | 2.0309 |
| 1.00E+11 | 2.5538 | 1.00E+10 | 1.3518 |

[a]Phage clones prepared with type 33 bacteriophage M13 vector containing wild type g.III gene (does not encode L8P and S11P substitutions).
[b]Phage clones prepared with type 33 bacteriophage M13 vector containing mutated, wild type g.III gene encoding L8P and S11P substitutions.

The $OD_{650}$ values in Table 6 demonstrate that when using a type 33 bacteriophage M13 vector containing mutations that encode L8P and S11P substitutions in the mature, wild type g.III gene product, increased expression of a Fab fused (via a peptide spacer) to the P.III surface protein encoded by the recombinant g.III gene is obtained.

Sequence Listing

SEQ ID NO: 1 (mature phage M13 surface protein P.III, encoded by recombinant and
WT g.III gene (without signal peptide))
AETVESCLAKSHTENSFTNVWKDDKTLDRYANYEGCLWNATGVVVCTGDETQCY
GTWVPIGLAIPENEGGGSEGGGSEGGGSEGGGTKPPEYGDTPIPGYTYINPLDGTYPP
GTEQNPANPNPSLEESQPLNTFMFQNNRFRNRQGALTVYTGTVTQGTDPVKTYYQY
TPVSSKAMYDAYWNGKFRDCAFHSGFNEDLFVCEYQGQSSDLPQPPVNAGGGSGG
GSGGGSEGGGSEGGGSEGGGSEGGGSGGGSGSGDFDYEKMANANKGAMTENADE
NALQSDAKGKLDSVATDYGAAIDGFIGDVSGLANGNGATGDFAGSNSQMAQVGDG
DNSPLMNNFRQYLPSLPQSVECRPFVFGAGKPYEFSIDCDKINLFRGVFAFLLYVATF
MYVFSTFANILRNKES

Sequence Listing

SEQ ID NO: 2 (mature, mutated phage M13 surface protein P.III (L8P + S11P amino
acid substitutions) encoded by mutated wild-type g.III (without signal peptide))
AETVESCPAKPHTENSFTNVWKDDKTLDRYANYEGCLWNATGVVVCTGDETQCYG
TWVPIGLAIPENEGGGSEGGGSEGGGSEGGGTKPPEYGDTPIPGYTYINPLDGTYPPG
TEQNPANPNPSLEESQPLNTFMFQNNRFRNRQGALTVYTGTVTQGTDPVKTYYQYT
PVSSKAMYDAYWNGKFRDCAFHSGFNEDLYVCEYQGQSSDLPQPPVNAGGGSGGG
SGGGSEGGGSEGGGSEGGGSGGGSGSGDFDYEKMANANKGAMTENADEN
ALQSDAKGKLDSVATDYGAAIDGFIGDVSGLANGNGATGDFAGSNSQMAQVGDGD
NSPLMNNFRQYLPSLPQSVECRPFVFGAGKPYEFSIDCDKINLFRGVFAFLLYVATFM
YVFSTFANILRNKES SEQ ID NO: 3 (nucleotide sequence of recombinant g.III gene (without signal peptide-
encoding sequence))
gccgagacagtggagagagcctggccaagttcgcacaccgagaacagatcaccaatgttggaaggatgataagaccctggaccg
ctatgccaattacgaaggttgcttatggaacgcaaccggtgtggttgtgtgcacaggcgatgagacccaatgctatggcacctgggtg
ccgatcggtctggcaattccggagaacgaaggcggaggtagcgaaggaggtggaagtgaaggcggaggatcggaagggggtgg
cacaaagccaccagaatatggagacaccccgattccagatttacacctacattaatccgctggatggtatacaccaccaggcaccgaa
cagaatccggcaaacccgaacccgagcctggaagaaagccaaccgctgaacacatttatgttccaaaacaaccgttttcgtaaccgtc
aaggagccctgaccgtatacaccggtacagtgacccaggtacagatccggtgaagacctactatcaatatacaccggttagcagca
aggcaatgtacgatgcatattggaatggcaagtttcgtgattgtgcatttcaatgaagacctgttttgtgtgcgaataccaa
gggtcagagcagcgattTaccgcagccaccggttaacgcaggtggtggaagcggaggggaagtggcggtgggtcagaaggcg
gaggatcggaaggaggtgggagtgaaggagggggaagcgaaggaggggatcaggaggtggtagcggaagtatgcatacttcata
ctacgagaagatggccaatgcaaacaaaggcgcaatgacagagaacgcagacgagaatgcactcaaagtgatgcaaaggggtaa
gctggacagcgttgcaaccgactatggagcagcaattgacggctttatcggagatgtcagcggtctggcgaacggcaacggagcaa
caggcgacttcgcaggtagcaacagccagatggcacaggttgatagatggcgacaacagtccgctgatataacaactttcgccagtac
ctgccgagtctgccacaaagcgtcgagtgccgtccgtttgttttcggtcaggcaagccgtacgagttcagcatcgactgcgataagat
taatctttttcgcggagttttcgcattcctgctgtacgtggcaacgttcatgtacgttttcagcaccttcgccaatatcttacgcaacaaaga
aagc SEQ ID NO: 4 (nucleotide sequence of mutated, wild-type g.III gene (encoding L8P +
S11P amino acid substitution) (without signal peptide-encoding sequence))
gccataaaactgttgaaagttgtccatgcaaaaccccatacagaaaattcatttactaactatctgtgaaagacgacaaaactttagatcgttac
gctaactatgagggctgtctgtggaatgctacaggcgttgtagtttgtactggtgacgaaactcagtgttacggtacatgggttcctattg
ggcttgctatccctgaaaatgagggtggtggctctgagggtggcggttctgagggtggcggttctgagggtggcggtactaaacctcc
tgagtacggtgatacacctattccgggctatacttatatcaaccctacatacggcacttatccgcctggtactgagcaaaaccccgctaa
tcctaatccttctcttgaggagtctcagcctcttaatactttcatgtttcagaataataggttccgaaataggcaggggcattaactgtttat
acgggcactgttactcaaggcactgaccccgttaaaaacttattaccagtacactcctgtatcatcaaaagccatgtatgacgcttactgga
acggtaaattcagagactgcgctttccattaggctttaatgaggatttatttgtttgtgaatatcaaggccaatcgtctgacctgcctcaac
ctcctgtcaatgctggcggcggctctggtggtggttctggtggcggctctgagggtggtggctctgagggtggcggttctgagggtgg
cggactgaggatagatcgatttccggtggtggctctggttccggtgattttgattatgaaaagatggcaaacgctaataagatgggctatg
accgaaaatgccgatgaaaacgcgctacagtctgacgctaaaggcaaacttgattctgtcgctactgattacggtgctgctatcgatgg
tttcattggtgacgtttccggccttgctaatggtaatggtgctactggtgattttgctggctctaattcccaaatggctcaagtcggtgacgg
tgataattcacattaatgaataatttccgtcaatatttaccttcccctccctcaatcggttgaatgtcgcccttttgtattggcgaggtaaacc
atatgaattttctattgattgtgacaaaataaacttattccgtggtgtctttgcgtttctttatatgttgccacctttatgtatgtatttcttacgttt
gctaacatactgcgtaataaggagtct SEQ ID NO: 5 (nucleotide sequence of wild-type g.III gene (without signal peptide-
encoding sequence))
gccgaaactgttgaaagttgtgatagcaaaaatcccatacagaaaattcattactattgtctggaaagacgacaaaactttagatcgttacg
ctaactatgagggctgtctgtggaatgctacaggcgttgtagtttgtactggtgacgaaactcagtattttggtacatgggttcctattgg
gcttgctatccctgaaaatgagggtggtggactgagggtggcggttctgagggtggcggttagagggtggcggtactaaacctcct
gagtacggtgatacacctattccgggctatacttatatcaaccactcgacggcatttatccgcctggtactgagcaaaaccccgctaat
cctaatccttctcttgaatgattctcatcctcttaatactttcatgtttcagaataataggttccgaaataggcaggggcattaactatttttata
cgggcactgttactcaaggcactgaccccgttaaaacttattaccagtacactcctgtatcatcaaaagccatgtatgacgcttactggaa
cggtaaattcagagactgcgctttccattaggctttaatgaggatttatttgtttgtgaatatcaaggccaatcgtctgacctgcctcaacct
cagtcaatgaggcggcggctctggtggtggttaggtggcggctctatagatgtatgtatgctctgagggtggcggttagagggtggc
ggctctgagggaggcggaccggtggtggctctggttccggtgattttgattatgaaaagatggcaaacgctaataagggggctatga
ccgaaaatgccgatgaaaacgcgctacagtctgacgctaaaggcaaacttgattctgtcgctactgattacggtgctgctatcgatggt
tcattggtgacgtttccggccttgctaatggtaatggtgctactggtgattttgctggctctaattcccaaatggctcaagtcggtgacggt
gataattcacctttaatgaataatttccgtcaatatttaccaccctccctcaatcggttgaatgtcgcccttttgtcttggcgctggtaaacc
atatgaattttctattgattgtgacaaaataaacttattccgtggtgtctttgcgttttatttatatgttgccacctttatgtatgtatttctacgttt
gctaacatactgcgtaataaggagtct SEQ ID NO: 6 (nucleotide sequence for parental type-33 plasmid with recombinant
and wT g.III gene (without L8P and S11P encoding mutations) (including signal
peptide-encoding sequences))
aatgctactactattagtagaattgatgccaccattcagctcgcgccccaaatgaaaatatagctaattaggttattgaccatagcgaaa
tgtatctaatggtcaaactaaatctactcgttcgckataattgggaatcatttgttatatggaatgaaacttccagacaccgtactttagttgc
atatttaaaacatgttgagctacagcattatattcagcaattaagctctaagccatctgcaaaaatgacctcttatcaaaggagcaattaa
aggtactctctaatcctgacctattggagtttgcttccgattctggttcgctttgaagctcgaattaaattgcgatatttgaagtctttcgggc
ttcctataatcttttttatatgcaatccgctttgatctgactataatagtcagggtaaagacctgattttatattttatggtcattacgttttctgaa
ctgataaagcattgaggggattatattatgactgaacgaagtcacgtcagtctaaaaggcttctcgctatttggtttttatcgtcgtctggtaaacgagggttatgatagttgttctcttactatgcct
cgtaattcctttgatcgttatgtatctatcattagttgaatggtgattcctaaatctcaactgatgaatatctacctgtaataatgttgttccgtt
agttcgattattattgtagatttttcttcccaacgtcctgactggtataatgagccagttcttaaaatcgcataaggtaattcacaatgattaa
agtgaaatttaaaccatctcaagcccaattactactcgttctggtgtttctcgtcagggcaagccttattcactgaatgagcagctttgtta
cgttgatttgggtaatgaatatccggttcttgtcaagattactcttgatgaaggtcagccagcctatgcgcctggtagtacaccgttcatct

Sequence Listing

```
gtcctcatcaaagttggtcagttcggttcccttatgattgaccgtctgcgcctcgttccggctaagtaacatggagcaggtcgcggatttc
gacacaatttatcagatcgatgatacaaataccgttgtactttattttcgcatcttggtataatcatagggatgtcaaagatgagtgttttagtgt
attatttgcctctttcgttttaggttggtgccttcgtagtggcattacgtattttacccgtttaatggaaacttcctcatgaaaaagtattagtc
ctcaaagcctctgtagccgttgctaccctcgttccgatgctgtctttcgctgctgagggtgacgatcccgcaaaagcggcctttaactcc
ctgcaagcctcagcgaccgaatatatcggttatgcgtgqtcgatggttgttgtcattgtcggcgcaactatcggtatcaagctattttaag
aaattcacctcgaaagcaagctgataaaccgatacaattaaaggctccttaggagcctttttttttggaptttttcattgtgaaaaaattatt
attcgcaattcattagttgttcctttctattctcactccgccgaaactgttgaaagttgtttagcaaaatcccatacagaaaattcatttactaa
cgtctggaaagacgacaaaactttagatcgttacgctaactatgagggctgtagtggaatgctacaggcgttgtagtttgtactggtga
cgaaactcagtgttacggtacatgggttcctaagggcttgctatccctgaaaatgagggtggtggctctgagggtggcggttctgagg
gtggcggttctgagggtggcggtactaaacctcctgagtacggtgatacacctattccgggctatacttatatcaacctctcgacggca
cttatccgcctatgtactgagcaaaaccccactaatcctaatcctcttacttgaggagtctcagcctataatactacatgatcagaataata
ggttccgaaataggcaggggggcattaactgtttatacgggcactgttactcaaggcactgaccccgttaaaacttattaccagtacactc
ctgtatcatcaaaagccatgtatgacgcttactggaacggtaaattcagagactgcgcttccattctggattaatgaggatttatagtag
tgaatatcaaggccaatcgtctatacctgcctcaacctcctgtcaatgctatgcatgcggctaggtggtggttctggtggcggctctgagg
gtagtagctctgagggtggcggttctgagggtggcggctagagggaggcggttccggtggtggctctggttccggtgatatgattat
gaaaagatggcaaacgctaataaggggcctatgaccgaaaatgccgatgaaaacgcgctacagtagacgctaaaggcaaacttga
ttctgtcgctactgattacggtgctgctatcgatggtttcattggtgacgtttccggccttgctaatggtaatggtgctactggtgattttgct
ggctctaattcccaaatggctcaagtcggtgacggtgataattcacctttaatgaataatttccgtcaatatttaccttcctccctcaatcg
gttgaatgtcgcccttttgtattggcgaggtaaaccatatgaattttctattgattgtgacaaaataaacttattccgtggtgtctttgcattt
cttttatatgttgccacattatgtatgtatttttcacgtttgctaacatatcggctaataaggagtcttaatcatgccagttattttgggtattccg
ttattattgcgtttcctccggtaccactggtaactagttcggctatctgcttacttactaaaaagggcttcggtaagatagctattgctatttc
attgtttcttgctatatattgggcttaactcaattcttgtatggttatctctatatattagcgctcaattacccctagactttgttcagggtgttc
agttaattctcccgtctaatgcgcttcctgttttatgttattctctgtaaaggctgctattttcattttgacgttaaacaaaaaatcgtttctt
atttggattgggataaataatatggctgtthattagtaactggcaaattaggctctagaaagacgctcgttagcgagggtaagattcaggat
aaaattgtagctgggtgcaaaatagcaactaatcttgatttaaggcttcaaaacctcccgcaagtcgggaggttcgctaaaacgcctcg
cgttcttagaataccggataagccttctatatctgatttgcttgctattgggcgcggtaatgattcctacgatgaaaataaaaacggcttgct
tatttacgatgagtgcggtacttggtttaatacccatttatgataatgataaggaaagacagccgattattatattggtttctacatgctcgtaa
attaggatgggatattatttttcttgttcaggacttatctattgttgataaacaggcgcgttagcattagctgaacatgttgtttattgtcgtcgt
aggacagaattacttaccttagtcggtacttttatattctcttattactggctcgaaatgcctagcctaaattacatgttggcgttgttaaat
atggcgattacaattaagccctactatttgagcgttggctttatactatgtaagaattgtataacgcatatatatactaaacagatctttttctag
taattatgattccggtgtttattcttatttaacgccttatttcacacggtcggtatttcaaaccattaaatttaggtcagaagatgaagcttac
taaaatatatttgaaaaagattcacgcgttcctttgtcttgcgattggatttgcatcagcatttaccttagttatataaccaaactaagccgg
aggttaaaaaggtagtactcagaccatgattttgataaattcactattgactatctcagcgtcttaatctaagctatcgctatgttttcaag
gattctaagggaaaattaattaatagcgacgatttacagaagcaaggttattcactcacatatattgatttatatactgtttccattaaaaag
gtaattcaaatgaaattgttaaatgtaattaattttgttttcttgatgtttgtttcatcatatcttttgacaggtaattgaaatataataattcgcct
ctgcgcgattttgtaacttgg-tattcaaagcaatcaggcgaatccgttcattgttctcccgatgtaaaaggtactgttactgtatattcatag
acgttaaacctgaaaatctacgcaattattattttagttttacgtgcaaatgattttgataatagtaggactaaccatccattattcagaagt
ataatccaaacaatcaggattatattgatgaattgccatcatctgataatcaggaatatgatgataattccatctccttaggtggtttattgtt
ccgcaaaatgataatgttactcaaacttttaaaattaataacgttcgggcaaaggatttaatacgagttgtcgaattgtttgtaaagtctaata
cactaaatcacaaatatattatctattgacggctctaatctattagttgttagtgacctaaagatattttagataaccttcctcaattccttttca
actgttgatttgccaactgaccagatattgattatagatgttttgaatgttcgacaaggtgatgcttttagattttttcatttgagctgatctc
tcagcgtggcactgttgcaggcggtgttaatactgaccgcctcacctctgttttatcttctgctggtggttcgttcggtatttttaatggcgat
gattagggctatcagttcgcgcattaaagactaatagccattcaaaaataagtctgtgccacgtattcttacgattcaggtcagaagggt
tctatctctgttggccagaatgtcccttttattactggtcgtgtgactggtgaatctgccaatgtaaataatccatttcagacgattgagcgtc
aaaatgtaggtatttccatgagcgtttttcctgttgcaatggctggcggtaatattgttctggatattaccagcaaggccgatagtttgagtt
cttctactcaggcaagtgatgttattactaatcaaaataagtattgctacaacggttaattgcgtgatgacagactctttactcgattgatcc
tcactgattataaaaacacttctcaggattctggcgtaccgttcctgtctaaaatccctttaatcggcctcctgtttagctcccgctctgattct
aacgaggaaagcacgttatacgtgctcgtcaaagcaaccatagtacgcgccctgtagcggcgcattaagcgcagcgggtgtggtgg
ttacgcgcagcgtgaccgctacacttgccagcgccctagcgcccgctccttcgctactttccgctacttccctttcctcgcacgttcgccggatt
cccgtcaagctctaaatcgggggctccattagggttccgatttagtacatacggcacctcgaccccaaaaaacttgatttgggtgatg
gttcacgtagtgggccatcgccctgatagacggtattcgcctagacgttggagtccacgactttaatagtggactcttgaccaaactg
gaacaacactcaaccctatctcgggctattcttttgatttataagggattttgccgatttcggaaccaccatcacacaggattttcgcctgct
ggggcaaaccagcgtggaccgcttgctgcaactctctcagggccaggtgaaggcaatcagctgttgcccgtctcgctggtga
aaagaaaaaaccaccctggcgcccaatacgcaaaccgcctctccccgcgcgttggccgattcattaatgcagctggcacgacaggttt
cccgactatgaaagcgggcagtgagcgcaacgcaattaatgtgagttagacactcattaggcaccccaggctttgacactttatgcttcc
ggctcgtataatgtgtggaattgtgagcggataacaatttcacacgccaaggagacagtcataatgaaatacctattgcctacggcagc
cgctggattgttattactcgctgcccaaccagccatggccggcggaggataggcgagcaaaagctcattagtgaagaggatatacc
gagacagtatgaatagctgcctatgccaagtcatcacaccggaacagcttcaccaatgtttggaaggatgataagaaccgttgaccgcta
tgccaattacgaaggttgcttatggcagcaaccggtgttgttgtgtgcacaggcgatgagaccaatgctatggcacctgggtgccg
atcggtctggcaattccggagaacgaaggcggaggtagcgaaggaggtgaaagtgaaggcggaggatcagaaggggtggcac
aaagccaccagaatggagacaccccgattccaggttacacctacattaatccgctggatggtacatacctccaggcaccgaaca
gaatccggcaaaccccaaaccggccggtgaagaaagccaaccgctgaacacatttatgttccaaaaacaaccgttacgtaaccgtcaa
ggagccctataccgtatacaccggtcagtgaccccagggtcagatccggtgaagacctactatcaatacaccggttaatcagcaag
gcaatgtacgatgcatattggaatggcaagtttcgtgattgtgcatttcatagcggtttcaacgaagacctgtttgtgtgcgaataccagg
gtcagagcagcgatttaccgcagccaccggttaacgcaggtagtagaagcggaggggaagtggcggtgggtcagaaggcgga
ggatcggaaggaggtgggagtgaaggaggggggaagcgaaggagggggatcaggaggtggtagcgaagtggcgacttcgact
acgagaagatggcaatgcaaacaaaggcgcaatgacagagaagacagcgaataagtgactgcaaagggtaagc
tggacagcgttgcaaccgactatggagcagcaattgacggctttatcggagatgtcagcggtctggcgaacggcaacggagcaaca
ggcgacttcgcaggtagcaacagccagatggcacaggttggagatggcgacaacagtccgctgatgaacaactttcgccagtacct
gccgagtctgccacaaagcgtcgagtgccgtccgtttgttttcggtgcaggcaagccgtacgagttcagcatcgactgcgataagatta
atattttcatcggagttttcgcattcctgctgtacgtggcaacgtcatgtacgattcagcaccttcgccaatatcttacgcaacaaagaa
gctaagcaatagcgaaggagccccgaccgatcgccctcccaacagttgcgcagcctgaatggcgaatggcgcgacgcgccctgtagcggcgcattaagcgcggcgggtgtggtgg
ggcaccagaagcggtgccgaaagctggctggagtgcgatcttcctgaggccgatactgtcgtcgtccccctcaaactggcagatgc
acggttacgatgcgcccatctacaccaacgtgacctatcccattacggtcaatccgccgtttgttcccacggagaatccgacgggttgtt
actcgctcacatttaatgttgatgaaagaggctacaggaaggccagacgcgaattatattgatgcgttcctattggttaaaaaatgag
ctgatttaacaaaaatttaatgcgaattttaacaaaatattaacgtttacaatttaaatatttgcttatacaatcttcctgtttttgggcttactg
attatcaaccggggtacatatgattgacatgctagttttacgattaccgttcatcgattacttgtttgaccagactctcaggcaatgacctg
``` atagcctttgtagatctctcaaaaatagctaccctctccggcattaatttatcagctagaacggttgaatatcatattgatggtgatagactg
tctccggcattctcacccttttgaatcttacctacacattactcaggcattgcatttaaaatatatgagggttctaaaaatttttatcatgcgt
tgaaataaaggatctcccgcaaaagtattacagggtcataatgttttggtacaaccgatttagctttatgctagaggctttattgataatt
ttgctaattattgccttgcagtatgatttattggacgtt SEQ ID NO: 7 (c-myc detection tag amino acid sequence
EQKLISEEDL SEQ ID NO: 8 (nucleotide sequence encoding c-myc detection tag)
gagcaaaagctcattagtgaagaggatctt SEQ ID NO: 9 (Clone 18-24 IL-6 binding test peptide sequence
RTFCKEFGRYVADETYCAAL SEQ ID NO: 10 (nucleotide sequence encoding Clone 18-24 IL6 binding test peptide)
aggacttttgtaaggagtttgggcggtatgttgcggatgagacgtattgtgctgcgctt SEQ ID NO: 11 (Clone 18-22 IL-6 binding test peptide sequence)
ISLCDQPYVKSLNLPLCPLA SEQ ID NO: 12 (nucleotide sequence encoding Clone 18-22 IL-6 binding test peptide)
atttattgtgtgatcagccgtatgttaagagtcttaatcttccgttgtgtccgcttgct SEQ ID NO: 13 (Clone 18-4 iL-6 binding test peptide sequence)
PPLCSWPAYQKFGGPLCTLG SEQ ID NO: 14 (nucleotide sequence encoding Clone 18-4 IL-6 binding test peptide)
cctccgctgtgttcaggcctgcaatcagaagtttggtggtccgctgtgtacgcttggt SEQ ID NO: 15 (nucleotide sequence for type-33 plasmid with recombinant g.III and
mutated WT g.III gene (with L8P and S11P encoding mutations)(including signal
peptide-encoding sequences)
aatgctactactattagtagaattgatgccaccttttcagctcgcgccccaaatgaaaatatagctaaacaggttattgaccatttgcgaaa
tgtatctaatggtcaaactaaatctactcgttcgcagaattgggaatcaactgttatatggaatgaaacttccagacaccgtactttagttgc
atatttaaaacatgttgagctacagcattatattcagcaattaagttttaagccatctgcaaaaatgacctatatcaaaaggagcaattaa
atgtactctctaatcctgacctgttggagtttgatccatgtaggttcatcatgaagctcgaattaaaaacgcgatatttgaagtcttcatggc
ttcctcttaatattttgatgcaatccgattgcactgactataatagtcaggtaaagacctgatttttgatttatggtcattctcgttttctgaa
ctgtttaaagttatttgagggggattcaatgaatatttatgacgattttcaagtattggattgtttatccagtctaaacattttactgttaccccct
aggcaaaacttcattgcaaaagcctacgctattaggtattatcgtcgtaggtaaacgagggtatatatagtgagctcttactatgcct
cgtaattccattggcgttatgtatctgcttttagttgaatgtggtattcctaattttttcaactgatgaatctttctacctgtatttaatgttgttccgtt
agttcgtttattaacgtagatttttcttcccaacgtcctgactggtataatgagccagttcttaaaatcgcataaggtaattcacaatgattaa
agttgaaattaaaccatctcaagcccaatttactactcgactggtgtttctcgtcagggcaagccttattcactgaatgagcagctttgtta
cgttgatttgggtaatgaatatccggttcttgtcaagattactcttgatgaaggtcagccagcctatgcgcctggtctgtacaccgttcatct
gtcctctttcaaaatttggtcagttcggttccatatgattgaccgtctgcgcctcgttccatgctaagtaacatatgatcaggtcgcggatttc
gacacaattatcaggcgatgataaaatctccgttgtactttgtttcgccgtataactcgaggggggtcaaagatgagtgttttagtgt
attcttttgcctcatcgttttaggttggtgccttcgtagtggcattacgtatttacccgtttaatggaaacttcctcatgaaaaagtctttagtc
ctcaaagcactgtagccgttgctaccacgttccgatgctgtctttcatctgagagggtgacatatcccgcaaaagcgatcctttaactcc
ctgcaagcctcagcgaccgaatatatcggttatgcgtgggcgatagtgttgtcattgtcggcgcaactatcggtatcaagctgataag
aaattcacctcgaaagcaagctgataaaccgatacaattaaaggctccttttttttggagatttttcaacgtgaaaaaattatt
attcgcaattccttttagttgttcattctattacactccgccgaaactgttgaaagttgtccggcaaaacccatacagaaaattcatttact
aacgtctggaaagacgacaaaactttagatcgttacgctaactatgagggctgtctgtggaatgctacaggcgagtagatgtactggt
gacgaaactcagtgttacggtacatgggttcctattgggcttgctatccctgaaaatgagggtagtggctagagggtggcggttctga
gggtggcggttctgagggtggcggtactaaacctcctgagtacggtgatacacctattccgggctatacttatatcaaccctacgacg
gcacttatccgcctggtactgagcaaaaccccgctaatcctaatccactcttgaggagtctcagcctcttaatactttcatgatcagaata
ataggttccgaaataggcaggggcattaactgtttatacgggcactgttactcaagatcactgaccccgttaaaacttattaccagtaca
ctcctgtatcatcaaaagccatgtatgacgcttactggattggtaaattcagagactgcgattccattctggctttaatgagggatttatttgt
ttgtgaatatcaaggccaatcgtctgacctgcctcaacctcctgtcaatgctggcggcggctcggtggtggttctggtagcggctctga
gggtggtggctctgagggtggcggttctgagggtggcggctctgaggggtggcggttctgagggtggcggtgattttgat
tatgaaaagatggcaaacgctaataagggggctatgaccgaaaatgccgatgaaaacgcgctacagtctgacgctaaaggcaaactt
gattctatcgctactgattacggtgctgctatcgatggtttcattggtgacgtttccggccttgctaatggtaatggtgctactggtgattttg
ctggctctaattcccaaatggctcaagtcggtgacggtgataattcaccttttaatgataattccgtcaatatttaccttccctccctcaatc
ggttgaatgtcgcccttttgtcttggcgctggtaaaccatatgaattttctattgattgtgacaaaataaacttattccgtggtgtctttgcgtt
tcttttatatgttgccacctttatgtatgtattttctacgtttgctaacatactgcgtaataaggagtcttaatcatgccagttcttttgggtattcc
gttattattgcgtttcctcggtttccttctggtaactttgttcggctatagcttacttttcttaaaagggatcggtaagatagctattgctatttc
attgtttcttgctcttattattgggcttaactcaattcttgtgggttatctctctgatattagcgctcaattaccctctgactttgttcagggtgtt
cagttaattctcccgtcaatgcgcttccctgttttatgttattactagtaaaggagctatttttcatttagacgttaaacaaaaaatcgtttc
ttatttggattggtataaataattggtttattttgtaactgcaaattaggctctgaaagacgctcgttagcgttggtaagattcaatg
ataaaattgtagctgggtgcaaaatagcaactaatctgatttaaggcttcaaacctcccgcaagtcggagggttcgctaaaacgcctc
gcattatagaataccggataagcctctatatagatttgcttgctattgggcgcggtaatgattcctacgatgaaaataaaaacggcttg
cttgttctcgatgagtgcggtacttggtttaatacccgttcttggaatgataaggaaagacagccgattattgattggtttctacatgctcgt
aaattaggatgggatattatUtcttgttcaggacttatctattgttgataaacaggcgcgttctgcattagctgaacatgagtttattgtcgt
cgtctgatacagaattacttttacctttgtcgtatctttattactgtctcttattactggctgcgaaaatgcctctgcctaaattacatgttggcgttgtt
aaatatggcgattctcaattaagccctactgttgagcgttggattactagctggtaagaatttgtataacgcatatgatactaaataggatttt
ctagtaattatgattccggtgtttattatatttaacaccttatttatcacacggcggtatttcaaaccattaaatttaggtcagaagatgaag
cttactaaaatatatttgaaaaagttttcacgcgttcttttgtcttgcatattggatttgcatcagcatttacatatagttatataacccaacctaag
ccggaggttaaaaaggtagtctctcagacctatgattttgataaattcactattgactcttctcagcgtcttaatctaagctatcgctatgtat
caaggattctaagggaaaattaattaatagcgacgatttacagaagcaaggttattcactcacatatattgatttatgtactgtttccattaaa

Sequence Listing

```
aaaggtaattcaaatgaaattgttaaatgtaattaattttgttttcttgatgtttgtttcatcatcttatttgctcaggtaattgaaatgaataattc
gcctagcgcgattagtaacttggtattcaaagcaatcaggcgaatccgttattgtttctcccgatgtaaaaggtactgttactgtatattca
tctgacgttaattctgaaaatctacgcaatttctttatttctgattacgtatcaaatatattttgatatatgtaggttctaaccttccattattcaga
agtataatccaaacaatcaggattatattgatgaattgccatcatctgataatcaggaatatgatgataattccgctccttaggtggtttatt
gttccgcaaaatgataatgttactcaaacttttaaaattaataacgttcgggcaaaggatttaatacgagttgtcgaattgtagtaaagtcta
atacttctaaatcacaaatattattatctattgacatgctctaatctattagttgttagtatctcctaaagatattttagataaccttcctcaattcctt
tcaactgttgatttgccaactgaccagatattgattgagggtttgatattttgaggttcagcaaggtgatgctttagattttttcatttgctgctgg
ctctcagcgtggcactgttgcaggcggtgttaatactgaccgcctcacctctgttttatcttctgctggtggttcgttcggtatttttaatgg
gatgttttagggctatcagttcgcgcattaaagactaatagccattcaaaaatattgtagtgccacgtattcttacgctttcaggtcagaag
ggttctatctctgttggccagaatgtccctttattactggtcgtgtgactggtgaatctgccaatgtaaataatccatttcagacgattgagc
gtcaaaatgtagattatttccatgagcgtattcctgttgcaatggctggcggtaatattgttctgatattaccagcaaggccgatagtttga
gttcttctactcaggcaagtgatgttattactcaaagaagtattgctacattggttaatttgcgtgatggacagactcttttttactcggtg
gcctcactgattataaaaacacttacaggattaggcgtaccgttcagtctaaaatccctttaatcggcctcagttagctcccactag
attctaacgaggaaagcacgttatacgtgctcgtcaaagcaaccatagtacgcgccctgagcggcgcattaagcgcatcatggtgtat
gtggttacgcgcagcgtgaccgctacacttgccagcgccctagcgcccactcctttcgctacttccatccatctcgccacgttcgccg
gctttccccgtcaagctctaaatcgggggctccctttagggttccgatttagtgctttacgggcacctcgaccccaaaaaacttgatttggg
tgatggttcacgtagtgqtccatcgccctgatagacggttttttcgccctttgacgttgatagtccacgttctttaatagtggactcttgttcca
aactggaacaacactcaacccctatctcgggctattcttttgatttataagggattttgccgatttcggaaccaccatcacacaggatttttcg
cdactggggcaaaccagcatgaccgcttgaacaactctctcagggccaggcggtgaagggcaatcagctattgccgtctcgct
ggtgaaaagaaaaaccaccctggcgcccaatacgcaaaccgcctctccccgcgcgttggccgattcattaatgcagctggcacgac
aggtttcccgactggaaagcgggcagtgagcgcattgcaattaatgtgagttagctcactcattaggcacccaggcttgacactttat
gatccggctcgtataatgtgtggaattgtgagcggataacaattcacacgccaaggagacattcataatgaaatacctattgcctacg
gcagccgaggattgttattactcgagcccaaccagccatggccggcggaggatctggcgagcaaaagctcattagtgaagaggat
cttgccgagacagtggaagctgcctggccaagtcgcacaccgaagcttcaccaatgtttggaaggatgataagaccagga
ccgctatatccaattacgaagatttgatatggaacatcaaccatgattgatttgtgtgcacaggcggatgagacccaatgctatggcacctgat
gtgccgatcggtctggcaattccggagaacgaaggcggaggtagcgaaggaggtggaagtgaaggcggaggatcggaaggggg
tggcacaaagccaccagaatatggagacaccccgattccaggRacacctacattaatccgaggatggtacatacccctccaggcacc
gaacagaatccggcaaaccgagcctggaagaaaagccaaccgctgaacacatttatgttccaaaacaaccgttttcgtaac
cgtcaaggagccctgaccgtatacaccggtacagtgacccagggtacagatccggtgaagacctactatcaatatacaccggttagc
agcaaggcaatgtacgatgcatattggaatggcaagtttcgtgattgtgcatttcatagcggttttcaacgaagacctgtttgtgtgcgaat
accagggtcagagcagcgatttaccgcagccaccggttaacgcaggtggtggaagcggaggggggaagtggcggtgggtcagaag
gcggaggatcggaaggaggtgagagtgaaggaggggggaagcgaaggaggggggatcaggaggtggtagcggaagtggcgactt
cgactacgagaagatggccaatgcaaacaaaggcgcaatgacagaagcactgcaaagtgatgcaaagg
taagctggacagcgttgcaaccgactatggagcagcaattgacggctttatcggagatgtcagcggtctatgcgaacggcaacggag
caacaggcgacttcgcaggtagcaacagccagatggcacaggttggagatggcgacaacagtccgctgatgaacaactttcgccag
tacctgccgagtctgccacaaagcgtcgagtgccgtccgtttgttttcggtgcaggcaagccgtacgagttcagcatcgactgcgataa
gattaatctUttcgcgcgagttttcgcattcctgctgtacgtggcaacgttcatgtacgttttcagcaccttcgccaatatcttacgcaacaaa
gaaagctaagcaatagcgaagaggccccaccgatcgcccttcccaacagttgcgcagcctgaatggcgaatggcgctttgcctgg
tttccggcaccagaagcggtgccggaaagaggctggagtgcgatcttcctgaggccgatactgtcgtcgtcccctcaaactatgcag
atgcacggttacgatgcgcccatctacaccaacgtgacctatccattacgtcaatccgccgtttgttcccacggagaatccgacggg
ttgttactcgctcacatttaatgttgatgaaagctggctacaggaaggccagacgcgaattatttttgatggcgttcctattggttaaaaat
gagctgatttaacaaaaatttaatgcgaattttaacaaaatattaacgtttacaatttaaatatttgatatacaatcttcctgttttttgggcttt
ctgattatcaaccggggtacatatgattgacatgctagttttacgattaccgttcatcgattctcttgtttgctccagactctcaggcaatgac
ctgatagcctttgtagatctctcaaaaatagctaccctctccaaagcttatcagctagaacggttgaatatcatattgatggtgatttga
ctgtctccggcattctcacccttttgaatcttttacctacacattactcaggcattgcatttaaaatatatgagggttctaaaaattttttatcatg
cgttgaaataaaggcttctcccgcaaaagtattacagggtcataatgtttttggtacaaccgatttagctttatgctctgaggctttattgctt
aatttttgctaattctttgccttgcctgtatgatttattggacgtt
```

SEQ ID NO: 16 (nucleotide sequence encoding Clone 18-24, 18-22, and 18-4 peptide linker)
ggcggaggataggc SEQ ID NO: 17 (nucleotide sequence encoding endogenous bacteriophage M13 P.III signal peptide)
gtgaaaaaattattattcgcaatcctttagttgttcattcattctcactcc SEQ ID NO: 18 (amino acid of endogenous bacteriophage M13 P.III signal peptide)
VKKLLFAIPLVVIPFYSHS SEQ ID NO: 19 (nucleotide sequence encoding pelB signal peptide)
atgaaatacctattgcctacggcagccgctggattgttattactcgctgcccaaccagccatggcc SEQ ID NO: 20 (pelB signal peptide)
MKYLLPTAAAGLLLLAAQPAMA SEQ ID NO: 21 (amino acid sequence of mature WT g.III gene product comprising L8P substitution) (without signal peptide))
AETVESCPAKSHTENSFTNNWKDDKTLDRYANYEGCLWNATGVVVCTGDETQCYG
TWVPIGLAIPENEGGGSEGGGSEGGGSEGGGTKPPEYGDTPIPGYTYINPLDGTYPPG
TEQNPANPNPSLEESQPLNTFMFQNNRFRNRQGALTVYTGTVTQGTDPVKTYYQYT
PVSSKAMYDAYWNGKFRDCAFHSGFNEDLFVCEYQGQSSDLPQPPVNAGGGSGGG
SGGGSEGGGSEGGGSGGGSEGGGSGGGSGSGDFDYEKMANANKGAMTENADEN
ALQSDAKCALDSVATDYGAAIDGFIGDVSGLANGNGATGDFAGSNSQMAVGDGD
NSPLMNNFRQYLPSLPQSVECRPFVFGAGKRYEFSIDCDKINLFRGVFTAFLLYVATFM
YVFSTFANILRNKES SEQ ID NO: 22 (amino acid sequence of mature WT g.III gene product comprising
S11P substitution) (without signal peptide)
AETVESCLAKPHTENSFTNWVKDDKTLDRYANYEGCLWNATGVVVCTGDETQCY
GTWVPIGLAIPENEGGGSEGGSEGGGSEGGGTKPPYGDTPIPGYTYINPLDGTYPP
GTEWNPANPNPSLEESQPLNTFMFQNNRFRNRQGALTVYTGTVTQGTDPVKTYYQY
TPVSSKAMYDAYWNGKFRDCAFHSGFNEDLFVCEYQGQSSDLPQPPVNAGGGSGG
GSGGGSEGGGSEGGGSEGGGSEGGGSGGGSGSGDFDYEKMANANKGAMTENAD
NALQSDAKGKLDSVATDYGAAIDGFIGDVSGLANGNGATGDFAGSNSQMAQVGDG
DNSPLMNNFRQYLPSLPQSVECRPFVFGAGKPYEFSIDCDKINLFRGVFAFLLYVATF
MYVFSTFANILRNIKES SEQ ID NO: 23 (nucleotide sequence encoding mature, WT g.III gene product
comprising L8P substitution (without signal peptide)
gccgaaactgtttgaaagttgtccggcaaaatcccatacagaaaattcatttactaacgtctggaaagacgacaaaactttagatcgttac
gctaactatgagggctgtctgtggaatgctacaggcgttgtagtttgtactggtgacgaaactcagtgttacggtacatgggttcctattg
ggcttgctatccctgaaaatgagggtggtggactgagggiggcggttcatagggatgcg,gttagagggtggcggtactaaacctcc
tgagtacggtgatacacctattccgggctatacttatatcaaccctctcgacggcacttatccgcctggtactgagcaaaaccccgctaa
tcctaatccttctcttgaggagtctcagcctcttaatactttcatgtttcagaataataggttccgaaataggcaggggcattaactgtttat
acgggcactgttactcaaggcactgaccccgttaaaacttattaccagtacactcctgtatcatcaaaagccatgtatgacgcttactgga
acggtaaattcagagactgcgctttccattctggctttaatgaggatttattttgtttgtgaataatcaaggccaatcgtctgacctgcctcaac
ctcctgtcaatgaggcggcggctaggtggtggttctggtggcggctctgtaggggtggtggctctgagggtggcggactgagggtgg
cggctctgagggaggcggttccggtggtggctctggttccggtgattttgattatgaaaagatggcaaacgctaataaggggctatg
accgaaaatgccgatgaaaacgcgctacagtctgacgctaaaggcaaacttgattctgtcgctactgattacggtgctgctatcgatgg
tttcattggtgacgtttccggccttgctaatggtaatggtgctactggtgattttgctggctctaattcccaaatggctcaagtcggtgacgg
tgataattcaccttaatgaataatttccgtcaatatttaccttccctccctcaatcggttgaatgtcgccctttgtctttggcgctggtaaacc
atatgaattttctattgattgtgacaaaataaacttattccgtggtgtctttgctttcttttatatgttgccaccttatgtatgtattttctacgttt
gctaacatactgcgtaataaggagtct SEQ ID NO: 24 (nucleotide sequence encoding mature, WT g.III gene product
comprising S11P substitution (without signal peptide)
gccgaaactgtataaagtattttagcaaaaccccatacagaaaattcatttactaacgtaggaaagacgacaaaactttagatcgttacg
ctaactatgagggctgtctgtggaatgctacaggcgttgtagtttgtactggtgacgaaactcagtgttacggtacatgggttcctattgg
gcttgctatccctgaaaatgagggtggtggctctgagggtggcggttctgagggtggcggttctgagggtggcggtactaaacctcct
gagtacggtgatacacctattccgggctatacttatatcaaccctctcgacggcacttatccgcctggtactgagcaaaaccccgctaat
cctaatccttctcttgaggagtctcagcctcttaatactttcatgtttcagaataataggttccgaaataggcaggggcattaactgtttata
cgggcactgttactcaaggcactgaccccgttaaaacttattaccagtacactcctgtatcatcaaaagccatgtatgacgcttactggaa
cggtaaattcagagactgcgattccattctggctttaatgaggatttattttgtttgtgaatatcaaggccaatcgtagacctgcctcaacct
cctgtcaatgctggcggcggctctggtggtggttctggtggcggctctgaggtggtggctctgagggtggcggttctgagggtggc
ggctctgagggaggcggttccggtggtggctctggttccggtgattttgattatgaaaagatggcaaacgctaataaggggctatga
ccgaaaatgccgatgaaaacgcgctacagtagacgctaaaggcaaacttgattctgtcgctactgattacggtgagctatcgatggtt
tcattggtgacgtttccggccttgctaatggtactggtgctactggtgattttgctggctctaattcccaaatggctcaagtcggtgacggt
gataattcacctttaatgaataatttccgtcaatatttaccttccctccctcaatcggttgaatgtcgccctttgtctttgcgaggtaaacc
atatgaattttctattgattgtgacaaaataaacttattccgtggtgtctttgtttcttttatatgttgccdcattatgtatgtattactacgat
gctaacatactgcgtaataaggagtct SEQ ID NO: 25 (Fab_HC amino acid sequence)
EVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTADDLDYW
GQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKAEPKSC SEQ ID NO: 26 (Fab_LC amino acid sequence)
DIQMTQSPSSLSASVGDRVTITCRASQGIRNYLAWYQQKPGKAPKLLIYAASTLQSG
VPSRFSGSGSGTDFTLTISSLQPEDVATYYCQRYNRAPYTFGQGTKVEIKRTVAAPSV
FIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC SEQ ID NO: 27 (nucleotide sequence encoding Fab_HC)
gaggtgcagctggtggagtctgggggaggcttggtacagcctggagggtccctgagactctcctgtgcagcctctggattcacctttg
atgactatgccatgcactgggtccgccaggctccagggaaggggctggagtgggtgtcagctattacaggaatagtggtcacataga
ctacgcagactccgtggagggccggttcaccataccagagacaatgccaagaactccctgtatagcaaatgaacagcagaggac
gaggacacggccgtatattactgtgcgaaagtgagctacctgagtactgaaccagcctggactactggggccaaggaaccttggt
caccgtctcctcagcctccaccaagggcccatcggtcttccccaggcaccacctccaagagcacctctggggcacagcggccct
gggctgcctgtcaaggactacaccccgaaccggtgacggtgtcgtggaactcaggcgccctgaccagcggcgtgcacaccncc
cggagtcctacagtartcaggactctactccctcagcagcgtggtgaccgtgccaccagcagcttgggcacccagacctacatctg
caacgtgaatcacaagcccagcaacaccaaggIggacaagaaagcagagcccaaatcagc SEQ ID NO: 28 (nucleotide sequence encoding Fab_LC)
gacatccagatgacccagtctccatcctccctgtctgcatctgtaggagacagagtcaccatcacttgccgggcgagtcagggcattc
gcaatttatagcctggtatcagcagaaaccagggaaagttcctaagctcctgatctatgctgcatccactagcaatcagggggtcccat
ctcggttcagtggcagtggatctgggacagatttcactctcaccatcagcagcctgcagcctgaagatgttgcaacttattactgtcatt
gctataaccgtgcccttacacgttcggccaagggaccaaggtggaaatcaaacgaactgtggctgcaccatctgtatcatcttccg
ccatctgatgagcagagaaatctgaaacgccctctgagtgtgcctgctgaataacttctatcccagagaggccaaagtacagtggaag
gtggataacgccctccaatcggtaactcccaggagagtgtcacagagcaggacagcaaggacagcacctacagcctcagcagca
ccctgacgctgagcaaagcagactacgagaaacaaagtctacgcctgcgaagtcacccatcagggcctgagctcgcccgtcaca
aagagcttcattaggggagagtgc -continued Sequence Listing SEQ ID NO: 29 (Pho A signal peptide)
VKQSTIALALLPLLFTPVAKA SEQ ID NO: 30 (nucleotide sequence encoding Pho A signal peptide)
gtgaaacaaagcactattgcactggcactcttaccgttactgtttaccccgtcgcaaaagcc SEQ ID NO: 31 (HA tag peptide)
YPYDVPDYAS SEQ ID NO: 32 (nucleotide sequence encoding HA tag peptide)
tacccgtacgacgttccggattatgccagc SEQ ID NO: 33 (Clone 18-24, 18-22, and 18-4 peptide linker amino acid sequence)
GGGSG SEQ ID NO: 34 (linker peptide)
AEAAAKEAAAKEAAAKA SEQ ID NO: 35 (linker peptide)
AEAAAKEAAAKEAAAKAGGGGS SEQ ID NO: 36 (linker peptide)
ALAAAKEAAAKEAAAKAGPPGP

I claim:

1. A type 33 bacteriophage M13 vector comprising a first polynucleotide sequence encoding a polypeptide sequence as given by SEQ ID NO:1 and a second polynucleotide sequence encoding a polypeptide sequence as given by SEQ ID NO:2.

2. The type 33 bacteriophage M13 vector according to claim 1 wherein said first polynucleotide sequence is given by SEQ ID NO:3 and said second polynucleotide sequence is given by SEQ ID NO:4.

3. The type 33 bacteriophage M13 vector according to claim 1 further comprising a polynucleotide sequence encoding a suitable detection tag sequence cloned in-frame with and upstream of the first polynucleotide sequence encoding the polypeptide sequence as given by SEQ ID NO:1.

4. The type 33 bacteriophage M13 vector according to claim 3 further comprising a polynucleotide sequence encoding an exogenous polypeptide, wherein the exogenous polypeptide is i) in-frame with and upstream of the detection tag or ii) in-frame with and in between the detection tag and the first polynucleotide sequence encoding the polypeptide sequence as given by SEQ ID NO:1.

5. The type 33 bacteriophage M13 vector according to claim 3, wherein the polynucleotide sequence encoding the suitable detection tag sequence encodes a c-myc tag, HA-tag, His-tag, Flag-tag, or a S-tag.

6. The type 33 bacteriophage M13 vector according to claim 5, wherein the polynucleotide sequence encoding the tag sequence encodes a c-myc tag.

7. The type 33 bacteriophage M13 vector according to claim 6 wherein the polynucleotide sequence encoding the c-myc tag is given by SEQ ID NO:8.

8. The type 33 bacteriophage M13 vector according to claim 1 wherein said vector comprises the polynucleotide sequence as given by SEQ ID NO:15.

9. The type 33 bacteriophage M13 vector according to claim 1 further comprising a polynucleotide sequence encoding an exogenous polypeptide cloned in-frame with and upstream of the polynucleotide sequence encoding the polypeptide sequence as given by SEQ ID NO:1.

10. The type 33 bacteriophage M13 vector according to claim 1 wherein said vector is a double stranded DNA molecule.

11. The type 33 bacteriophage M13 vector according to claim 1 wherein said vector is a double stranded DNA plasmid.

12. A method for producing a bacteriophage M13 particle comprising:
(a) transfecting a bacterial host cell with a double stranded type 33 bacteriophage M13 vector comprising a first polynucleotide sequence encoding a polypeptide sequence as given by SEQ ID NO:1 and a second polynucleotide sequence encoding a polypeptide sequence as given by SEQ ID NO:2,
(b) incubating said bacterial host cell under conditions suitable for expression of said first and second polynucleotide sequences and assembly of bacteriophage M13 particles in said bacterial host cell, and
(c) recovering from said bacterial host cell a bacteriophage M13 particle comprising polypeptide sequences given by the amino acid sequences of SEQ ID NO:1 and SEQ ID NO:2 independently displayed on the bacteriophage M13 coat surface.

13. The method according to claim 12 wherein said first polynucleotide sequence is given by SEQ ID NO:3 and said second polynucleotide sequence is given by SEQ ID NO:4.

14. The method according to claim 12 wherein the double stranded bacteriophage M13 vector further comprises a polynucleotide sequence encoding a suitable detection tag sequence cloned in-frame with and upstream of the first polynucleotide sequence encoding the polypeptide sequence as given by SEQ ID NO:1.

15. The type 33 bacteriophage M13 vector according to claim 14 further comprising a polynucleotide sequence encoding an exogenous polypeptide, wherein the exogenous polypeptide is i) in-frame with and upstream of the detection tag or ii) in-frame with and between the detection tag and the first polynucleotide sequence encoding the polypeptide sequence as given by SEQ ID NO:1.

16. The method according to claim 14, wherein the polynucleotide sequence encoding the suitable detection tag sequence encodes a c-myc tag, HA-tag, His-tag, Flag-tag, or and S-tag.

17. The method according to claim 16, wherein the polynucleotide sequence encoding the tag sequence encodes a c-myc tag.

18. The method according to claim 17 wherein the polynucleotide sequence encoding the c-myc tag is given by SEQ ID NO:8.

19. The method according to claim 12 wherein the double stranded M13 vector comprises the polynucleotide sequence as given by SEQ ID NO:15.

20. The method according to claim 12 wherein the double stranded M13 vector further comprises a polynucleotide sequence encoding an exogenous polypeptide cloned in-frame with and upstream of the polynucleotide sequence encoding the polypeptide sequence given by SEQ ID NO:1.

21. The method according to claim 12 wherein the bacterial host cell is an F+ bacterial strain.

22. A bacteriophage M13 particle wherein said particle comprises the polypeptides given by the amino acid sequences of SEQ ID NO:1 and SEQ ID NO:2 independently displayed on the phage particle coat surface.

23. The bacteriophage M13 particle according to claim 22 wherein said particle further comprises a suitable detection tag sequence fused to the N-terminus of the polypeptide sequence given by SEQ ID NO:1, optionally via a peptide linker.

24. The bacteriophage M13 particle according to claim 23 wherein the suitable detection tag sequence is given by SEQ ID NO:7.

25. The bacteriophage M13 particle according to claim 22 wherein said particle further comprises an exogenous polypeptide fused to the N-terminus of the polypeptide sequence given by the amino acid sequence of SEQ ID NO:1, optionally via a peptide linker.

26. The bacteriophage M13 particle according to claim 23 further comprising an exogenous polypeptide, wherein the exogenous polypeptide is fused to the N-terminus or the C-terminus of the suitable detection tag sequence, optionally, via a peptide linker.

* * * * *